(12) United States Patent
Lipman

(10) Patent No.: US 6,929,607 B2
(45) Date of Patent: Aug. 16, 2005

(54) COMPREHENSIVE PAIN ASSESSMENT SYSTEMS AND METHODS

(75) Inventor: Jonathon J. Lipman, Libertyville, IL (US)

(73) Assignee: Neuroscience Toolworks, Inc., Evanston, IL (US)

(*) Notice: Subject to any disclaimer, the term of this patent is extended or adjusted under 35 U.S.C. 154(b) by 266 days.

(21) Appl. No.: 09/841,795

(22) Filed: Apr. 24, 2001

(65) Prior Publication Data

US 2002/0052562 A1 May 2, 2002

Related U.S. Application Data

(63) Continuation-in-part of application No. 09/453,770, filed on Dec. 20, 1999, now Pat. No. 6,248,079.
(60) Provisional application No. 60/240,774, filed on Oct. 16, 2000.

(51) Int. Cl.$^7$ ................................ A61B 5/00
(52) U.S. Cl. ........................ 600/300; 604/500
(58) Field of Search ................. 600/300, 301, 600/557, 552–556; 607/46; 128/897, 898, 920, 923; 604/31, 65, 245

(56) References Cited

U.S. PATENT DOCUMENTS

| | | | |
|---|---|---|---|
| 2,728,337 A | | 12/1955 | Guillemin, Jr. |
| 4,641,661 A | | 2/1987 | Kalarickal |
| 4,884,091 A | | 11/1989 | Nakagomi |
| 5,022,407 A | | 6/1991 | Horch et al. |
| 5,025,796 A | | 6/1991 | Hargreaves et al. |
| 5,191,896 A | | 3/1993 | Gafni et al. |
| 5,230,345 A | | 7/1993 | Curran et al. |
| 5,293,876 A | | 3/1994 | Koltringer |
| 5,381,805 A | * | 1/1995 | Tuckett et al. ............ 600/557 |
| 5,474,084 A | | 12/1995 | Cunniff |
| 5,660,176 A | * | 8/1997 | Iliff ........................ 600/300 |
| 5,692,500 A | * | 12/1997 | Gaston-Johansson ...... 128/897 |
| 5,795,327 A | * | 8/1998 | Wilson et al. ............. 604/65 |
| 5,873,900 A | * | 2/1999 | Maurer et al. ............ 128/898 |
| 6,053,887 A | * | 4/2000 | Levitas et al. ............ 604/500 |
| 6,168,569 B1 | * | 1/2001 | McEwen et al. .......... 600/557 |
| 6,231,560 B1 | * | 5/2001 | Bui et al. ................. 604/500 |
| 6,241,704 B1 | * | 6/2001 | Peterson et al. .......... 604/31 |
| 6,416,480 B1 | * | 7/2002 | Nenov ..................... 600/300 |
| 6,529,195 B1 | * | 3/2003 | Eberlein .................. 600/557 |

FOREIGN PATENT DOCUMENTS

| | | |
|---|---|---|
| DE | 92 04 961.3 | 7/1992 |
| GB | 2 093 343 A | 9/1982 |

OTHER PUBLICATIONS

Johnson, Nelda, Measuring Health–Related Quality of Life: An Introduction to Survey Instruments, Formulary, Sep. 1998, vol. 33, pp. 897,898,903 & 904.*

(Continued)

*Primary Examiner*—Max F. Hindenburg
(74) *Attorney, Agent, or Firm*—Fitch, Even, Tabin & Flannery

(57) ABSTRACT

Systems, devices, and methods are provided for simultaneous assessment of a subject's subjective and objective pain states. These include a dolorimeter arrangement for determining a subject's cutaneous pain tolerance level at any site on the body. In certain preferred embodiments, the dolorimeter is hand-held and utilizes a sonar distance-measuring device. In another aspect, the systems, devices, and methods of the current invention include platforms effective for implementing pain monitoring methods that include delivering pain questionnaires to patients over a period of time points. The platforms may harvest analgesic drug data from nurses attending the patients, and may provide simple statistical analysis of collected data useful both at the bedside and at central base-stations. The platforms may provide additional functions based on analysis of patient pain data. Preferred embodiments of the current invention combine the dolorimeter arrangement with the platforms for implementing pain monitoring methods.

11 Claims, 18 Drawing Sheets

OTHER PUBLICATIONS

Togawa, Tatsuo, Patient Monitoring, Wiley Encyclopedia of Electrical Engineering and Electronics Engineering Online, Dec. 1999.*

Chapman, "On the Relationship of Human Laboratory and Clinical Pain Research," in Pain Measurement and Assessment, R. Melzack (ed.), Raven Press (NY), pp. 243–249 (1983).

Donovan, et al., "Incidence and Characteristics of Pain in a Sample of Medical–Surgical Inpatients," Pain 30:69–78 (1987).

Lipman, et al., "Chronic Pain Assessment Using Heat Beam Dolorimetry," Pain 30:59–67 (1987).

Lipman and Blumenkopf, "Comparison of Subjective and Objective Analgesic Effects of Intravenous and Intrathecal Morphine on Chronic Pain Patients by Heat Beam Dolorimetry," Pain 39:249–256 (1989).

Lipman, et al., "Normal and Radiculopathic Cutaneous Pain Tolerance Levels Evaluated by Heat–Beam Dolorimetry," J. Neurosurgery 72:883–888 (1990).

Lipman, "Pain Measurement," Chapter 9 in "Contemporary Issues in Pain Measurement." Parris, WCV (ed.) Kluwer Pubs., pp. 123–146 (1991).

Rollman, "Signal Detection Theory Pain Measures: Empirical Validation Studies and Adaptation–level Effects," Pain 6:9–21 (1979).

Sriwatanakul, et al.; "Analysis of Narcotic Analgesic Usage in the Treatment of Postoperative Pain," J. Am. Med. Ass'n. 250:926–929 (1983).

Svensson, et al., "Comparison of Four Laser Types for Experimental Pain Stimulation on Oral Mucosa and Hairy Skin," Lasers in Surgery and Medicine 11:313–324 (1991).

Svensson, et al., "Quantitative Determinations of Sensory and Pain Thresholds on Human Oral Mucosa by Argon Laser Stimulation," Pain 49:233–239 (1992).

Hardy et al., Pain Sensations and Reactions, pp. 67–77 (1952).

Information sheet entitled, "Model 33A and Model 33B Tail Flick Analgesy Meters", date unknown.

Jamison et al. "Electronic diaries for monitoring chronic pain: 1–year validation study", Pain 91:277–285 (2001).

* cited by examiner

TARGET

PAIN SEVERITY CATEGORY SCALE (PS)

PATIENT: CHECK THE BOX THAT BEST DESCRIBES
THE SEVERITY OF YOUR PRESENT PAIN

| NONE | A LITTLE | SOME | A LOT | TERRIBLE |
|------|----------|------|-------|----------|
|      |          |      |       |          |

FIG. 14

PAIN RELIEF CATEGORY SCALE (PR)

PATIENT: CHECK THE BOX THAT BEST DESCRIBES YOUR PRESENT PAIN RELIEF SINCE LAST SCORED

| | |
|---|---|
| NONE | ☐ |
| A LITTLE | ☐ |
| SOME | ☐ |
| A LOT | ☐ |
| COMPLETE | ☐ |

FIG. 15

COMPREHENSIVE PAIN ASSESSMENT SYSTEMS AND METHODS

The present application is a continuation-in-part of U.S. application Ser. No. 09/453,770, filed Dec. 2, 1999, now U.S. Pat. No. 6,248,079 (issued Jun. 19, 2001) which was based on and claimed the benefit of PCT/US00/41672, filed Oct. 27, 2000, which was based on and claimed the benefit of Provisional Application No. 60/240,774, filed Oct. 16, 2000), which are hereby incorporated by reference.

The invention described herein was funded, in part, by grant number R43NS34616 from the National Institutes of Health, under which the United States government has certain rights.

TECHNICAL FIELD

The present invention relates to neurological diagnostic tools including methods and devices for monitoring and managing patient pain.

BACKGROUND ART

Pain is the single most common symptom for which patients seek medical treatment and there is currently no objective method available for its measurement. Present methods of quantifying "pain" are little more than lexicons for its verbal description or biomechanical methods for measuring the restriction of a particular range of motion or activities of daily living associated with the pain. Some psychometric methods attempt to quantify the personality or cognitive distortions from which the pain patient suffers. In no case, however, do these methods reveal the covert and subjective sensory perception that is the pain experience in a way that can be quantified by an outside observer (for review, see Lipman J J. Chapter 9: Pain Measurement In: Contemporary Issues in Pain Management. Parris, WCV (ed.) KLUWER Pubs., (1991)). The need for pain measurement methods was recently addressed by both the Social Security Administration and the United States Congress. A report ordered by Congress through the Secretary of Health and Human Services by a Commission on the Evaluation of Pain, recommended that an objective measurement of pain be developed to assist in determining disability (see Fordice, *Back Pain in the Workplace: Management of Disability in Nonspecific Conditions-Task Force on Pain in the Workplace*, (I.A.S.P. Press, Seattle, 1995); Fields, *Core Curriculum for Professional Education in Pain: Task Force on Professional Education*, (I.A.S.P. Press, Seattle, 1995); American Pain Society, *Principles Of Analgesic Use In the Treatment of Acute Pain and Chronic Cancer Pain-a Concise Guide*, (American Pain Society, Washington D.C., 1990)).

The need for objective pain measurement goes beyond the economics of forensic disability assessment. Objective methods of pain measurement are required for accurate assessment of patient complaint and to assure appropriate treatment. For example, the need to appropriately medicate severe acute and chronic pain and also cancer pain requires an objective method of pain measurement. A corollary need is to avoid inappropriate treatment of pain—or claimed pain—where the possibility of malingering for secondary gain is a possibility. Such "secondary gains" are believed to account for an appreciable portion of chronic pain treatment demand, and forensically include the desire for disability payments, for insurance damage settlements or for other fiduciary incentives. Such secondary gains are not always conscious and may derive from psychological reasons related to the psychosocial set and setting of the patient and their disease. The inappropriate desire for opiate drugs probably accounts for a significant fraction of pain therapy prescription drug demand. Yet absent any objective method of establishing the existence of "pain", the physician has no objective standards by which to prohibit such demand, and frequently feels ethically bound to take claims of pain at face value, or risk accusation of ineffective care and inhumane treatment.

Furthermore, an objective pain measurement device that is operable in the general practitioner's office would fulfill a pressing diagnostic need. It is from the general practitioner's office that referrals to neurologists and other specialists are made. For example, patient complaints of subjective numbness are often not detectable on clinical examination because present diagnostic methods are not sensitive enough to detect the early stage sensory impairments of such neurological disorders as nerve root entrapment or peripheral neuropathy. As a result, patients with these types of neurological disorders cannot be diagnosed until the disorder progresses to a detectable level. The availability of a pain measurement device sensitive enough to detect the presence or absence of these and other abnormalities at an early stage would provide more effective medical intervention, or avoid unnecessary medical intervention. In order for such a device to be cost-effective for the general practitioner it should not require valuable dedicated space, and thus should be portable. Similarly, greater cost-effectiveness would be realized if the device were operable by a single person, unaided.

Basic psychophysical methods for the estimation of pain sensibility have a long history of questionable clinical relevance. Psychophysical methods seek to quantify pain intensity in an objective fashion despite the fact that pain is a complex and multi-faceted sensory mode, intrinsically containing dimensions of set, setting, ideation, memory, anxiety, and experiential import.

Subjective pain perception does not bear a simple relationship to stimulus intensity, but it nevertheless has some quantifiable dimensions and limits: a lower level of identity (the pain threshold) and an upper level of identity (the tolerance level). Below the pain threshold, stimuli of increasing intensity destined to broach this level are perceived as noxious yet non-painful (prepain). The pain threshold itself is highly labile and subject to psychological manipulation either of imposed suggestion (experimenter bias) or autosuggestion bias (the placebo response) or both. No studies have been able to demonstrate a relationship between pain threshold and the underlying pain state; in fact, pain threshold measurement procedures are unable to quantitatively demonstrate analgesic states engendered by clinically proven drugs as, for example, morphine (for review, see Chapman et al. "On the Relationship of Human Laboratory and Clinical Pain Research," *Pain Measurement and Assessment*, pp. 251–257 (Raven Press, New York, 1983)). Furthermore, the method suffers from major disadvantages when transferred to the clinical situation where the test subject, who may suffer excruciating pain of endogenous pathological origin, is less able to attend to the minor sensory nuances of the pain threshold.

The pain sensitivity range constitutes a psychophysical region between the pain threshold level, where prepain becomes subjectively painful, and the pain tolerance level, which represents the greatest intensity of a noxious stimulus that a subject can tolerate (Hardy, Wolff and Goodell in *Pain Sensations and Reactions* (Williams and Wilkins, Baltimore, 1952)). In contrast to the pain threshold level, the pain tolerance level is subjectively distinct and unequivocal.

Further, the pain tolerance level exhibits a linear change with stimulus intensity and yet it shares a sufficient commonality with the physiological processes of endogenous pathological pain perception that are positively influenced by changes in the endogenous pain state.

Pain tolerance levels are usually assessed by the use of a continuous, rather than a discrete, noxious stimulus, the cut-off of which is always the maximum limit of the subject's subjective pain tolerance. Pain tolerance has been measured by several means including the cold pressor test in which the hand or a limb is immersed in ice water until unendurable pain results, focal pressure, tourniquet ischemia and radiant heat (For review see Lipman J. J., "Pain Measurement," supra). Tolerance methods using these techniques, unlike threshold methods, also evoke some not inconsiderable anxiety and apprehension on the part of the subject, which may resemble the anxiety of the pain-suffering patient. However, studies have shown that tactile stimulation interferes with that aspect of cutaneous tolerance limit responsive to internal pain interference and thus methods that utilize a contact stimulus invalidate pain tolerance level results. Another method that has been developed uses hot air to generate heat in a subject (Muller et al., German Patent 92,04,961 (1992)). However, hot air, like the methods described above, generates contact stimulus, since heated moving air molecules stimulate mechanoreceptors found on the skin. Furthermore, this apparatus utilizes a temperature probe that makes contact with the skin near the site that is heated. Therefore, this apparatus cannot be used to accurately measure pain tolerance. While the cold pressor, focal pressure, tourniquet ischemia, and hot air tests all involve tactile stimulation, radiant heat methods do not require direct contact with the subject.

The concept of a radiant heat pain stimulator for human use was initially developed by Hardy, Wolff and Goodell in 1952 (*Pain Sensations and Reactions* (Williams and Wilkins, Baltimore, 1952)). However, most radiant heat pain stimulators have been designed to measure the pain threshold level and thus are prone to the disadvantages inherent in such measurement. Hargreaves et al. describe a radiant light/heat projector used as a thermal stimulator for use in testing both animals and man (U.S. Pat. No. 5,025,796 (1991)). However, all of the embodiments disclosed in Hargreaves et al., like the non-radiant heat apparatuses described above, involve tactile stimulation, since the subject must rest on a base to allow the radiant heat to be focused. Thus, pain tolerance results obtained with the instrument are invalid. Recently, a concept prototype heat pain stimulator was developed that measures the pain tolerance level (see Lipman et al., *Pain* 30, 59–67 (1987); Lipman et al., *Pain* 39, 249–256 (1989); and Lipman et al., *J. Neurosurg.* 72, 883–888 (1990)). The concept prototype was a nonportable, electromechanical device that did not allow for automatic data acquisition. As such, the concept prototype required dedicated laboratory space and also required one person to operate the device and a second person to record data. Accordingly, there remains a need in the art for a particular non-contact, radiant heat beam dolorimeter that provides a quantitative, objective measure of the pain tolerance level and allows for automatic data acquisition.

In applications such as a heat beam dolorimeter, where electromagnetic radiation (EMR) projected from an emitter is directed at a target, a feedback mechanism would be helpful to accommodate conditions where distance may undesirably change between emitter and target. Such a feedback mechanism might use a sensor, positioned at or within the target, to feedback-control either the power output or position (i.e., the emitter-target distance) of the emitter, thus ensuring that these characteristics of the emitter are rapidly and automatically adjusted to maintain target and/or sensor irradiation within set limits. Unfortunately, available sensor response characteristics are largely inadequate to this task. Thus, should a temperature sensor within the target be used to feedback control, for example, a motor-drive positioning mechanism on which a radiant heat projector (emitter) is mounted, whereby feedback from the sensor is used to control projector position, either toward or away from the target, it is found that accurate, rapid and responsive positioning of the emitter by the motor drive cannot be achieved because the sensor response time is invariably too slow, having too much inertia or resistance to change. The same is true of light and other forms of EMR. Therefore there is a need for automatic control processes that regulate the delivery rate of the EMR received at the target by adjusting the output of the emitter mechanism, the projector of heat or light or other EMR.

When the emitter is employed as a sensory stimulator for testing human cutaneous sensibility, such as a heat beam dolorimeter for determining pain tolerance as described above, it is essential that the energy delivered to the skin be precisely controlled. Since delivered energy is a proportional function of the power of the emitter and the distance of the emitter to the skin target, both must be held constant to achieve adequate stimulus control. Therefore, there is a need for improved automatic control processes that regulate the delivery rate of heat received at the target site of a patient's skin in heat beam dolorimeter applications. The present invention provides a sonar-based automatic-control system which overcomes these problems.

Pain management has only recently come into being as a specialty discipline in its own right; the American Academy of Pain Management (AAPM) was founded eleven years ago, for instance. Pain, described as an "epidemic" by AAPM, affects millions in the United States: 50 million Americans are partially or totally disabled by pain and 45% of all Americans seek care for persistent pain at some point in their lives (American Pain Society, American Academy of Pain Management, Janssen Pharmaceutical: Chronic pain in America: Roadblocks to relief, Study conducted by Roper Starch Worldwide (1999)).

The problem of undertreatment is however particularly topical since the recent introduction of new regulations governing hospital practice promulgated by the Joint Commission on Accreditation of Healthcare Organizations (JCAHO). These regulations came into force Jan. 1, 2001, and mandate clinic and hospital practices that are designed to both avoid undertreatment and to document affirmative medical pain-relief interventions. Health care providers must document their compliance with the directive. This invention provides an inexpensive computerized device, which meets these needs.

Educational initiatives are currently being introduced throughout both medical/nursing training and established practice to introduce the JCAHO mandates pertaining to clinical care. This initiative continues and enforces the earlier and continuing efforts of the International Association for the Study of Pain (IASP) and the AAPM into raising physician and nurse awareness of the need for humane treatment of pain and promoting the doctrine that pain is often unnecessary and avoidable with appropriate drug treatment. Specific recommendations include pre-emptive analgesic therapy, regular—timed—rather than PRN drug administration, and a general overhaul of historically unhelpful attitudes concerning the 'addictiveness' of opioids given for pain relief. (See, the management of chronic pain in older persons: AGS panel on chronic pain in older persons. J. Am. Geriatric Soc. 46(5):635–651 (1998)).

The core need in any pain management strategy is an effective method for assessing the subjective pain state of the patient, and of measuring changes in this state in response to treatment. Currently a variety of simple verbally administered or paper-and-pencil Pain Questionnaires (PQs) that the patient completes at intervals are used. Their currently remains a need for computerized PQ methods that satisfies the needs of both patients and health care providers, and simultaneously satisfies the JCAHO documentation requirements.

As described recently by Bellamy (1999) in a comparative evaluation of pain questionnaire methods, simple scaling methods (category and visual pain analog scales) are more responsive for assessment needs than complex ones (such as the McGill Pain Questionnaire) and defeat the latter's intercultural disadvantages of linguistic biases. (Bellamy, N. (1999) Comparative study of self-rating pain scales in osteoarthritis patients, Current Medical Research and Opinion 15(2):113–119). The demands of clinical practice further require that a pain assessment tool be (1) brief, (2) simple, (3) rapid to complete and (4) easy to score. (Bellamy N, Kaloni S, Pope J, Coulter K and Campbell J (1998) Quantitative rheumatology: A survey of outcome measurement procedures in routine rheumatology outpatient practice in Canada, J. Rheumatol. 25, 852–858; Bellamy N, Muirden K, Brooks P M et al (1998)). The JCAHO guidelines also provide that the method provide a measure of health-care provider compliance. It follows that the method should be capable of centralized data accession to this end. A final requirement suggested by the need to render the device practically useful to the nurse and physician is that it provides a statistical output of pain response to therapy both printable and immediately accessible at any time.

An early review of the need for, and the methods employed in, clinical pain measurement is found in Lipman et al. 1991. (Lipman J J. Chapter 9: Pain Measurement In: Contemporary Issues in Pain Management. Parris, WCV (ed.) KLUWER Pubs., (1991)). Pain, an entirely subjective phenomenon, is assessed either by indirect behavioral observation methods or by direct interrogation methods—the latter typically administered in the form of a pain questionnaire (PQ). These are of varying degrees of complexity—from the McGill Pain Questionnaire (MPQ) which takes about five to ten minutes to complete, to the simple Visual Pain Analog Scale (VPAS) which takes seconds to complete.

Pain questionnaire (PQ) methods seek to present the pain continuum as a metaphor—either linguistic, spatial, facial or otherwise—which the patient can endorse in such a manner as to relate the degree of their present pain or its relief. The range of metaphors is quite extensive, but in summary these are in typology either ordinal or category and either verbal or printed in form Verbal descriptor scales are commonly employed for pain assessment by asking the patient to rate their present pain on a numerical rating scale from one to one hundred or some other number: for instance, the NRS-101 asks the patient to scale their pain between one and a hundred and one but verbal enquiry has the serious disadvantage that the questioner (nurse or doctor) inevitably conveys expectation by voice, tone, facial expression, and demeanor, which will inevitably influence the patient's response. This face-to-face method is capable of engendering bias; indeed, it has been used by investigators studying the placebo response as a means of deliberately provoking the unconscious expectation of pain relief. (Lipman J J, Miller B E, Mays K S, Miller M N, North W C and Byrne, W L. (1990) Peak "B" Endorphin Concentration in Cerebrospinal Fluid: Reduced in Chronic Pain Patients and Increased During the Placebo Response. Psychopharmacology 109 (1) 112–116.) For this reason, in an attempt to place distance between the conscious or unconscious expectations of the questioner and the response of the patient, printed questionnaires are commonly preferred.

Printed ordinal metaphors such as the aforementioned visual pain analog or mood scales (VPAS or VMAS scales, respectively) provide on a printed page (or in the present case, a computer screen) a line (typically, historically and by convention 10 cm long) bounded by words that define the sensory continuum being measured. For the VPAS these words are, on the left, 'no pain' and on the right, 'maximum possible pain.' The patient indicates their present pain intensity by marking the line at the appropriate point (see FIGS. 2 and 4). By imposing index marks (usually 10, every centimeter or $\frac{1}{10}$th of the line) on the VPAS, the analog is converted into a category scale—with ten predetermined locations available for marking by the patient. Other category scales employ words arranged along a rank order continuum (e.g., 'no pain', 'a little', 'some', 'a lot', 'terrible') from which the patient may choose, and others employ nonlinguistic categories, such as the facial scale (used with pediatric or nonverbal patients) which presents a series of faces with stylized expressions representing the range from 'unhappy' at one end to 'happy' at the other.

One advantage of category scales when employed to ask the patient how they are feeling 'now' compared with 'before' (when they completed the scale previously) is that it is easy for the patient to recall their earlier response—limited as it was to a predetermined choice from a small number of choices. However, when used to ask the patient to rate their present degree of pain without regard to any earlier response they may have made, this property of category scales proves somewhat of a disadvantage—since it is hoped in this situation that the patient's present response will be uninfluenced by prior responses. For this reason, a simple unmarked 10 cm VPAS line is generally preferred for present pain assessment. Within certain limitations, the VPAS is a reliable way of polling opinion on a unidimensional axis and it has the advantage of being quick and easy to do, is easily understood by the patient, is readily scored (using a ruler when the test is printed) and has long been validated against other polling methods whilst retaining current validity and popularity (Scott J, Huskisson E C (1976) Graphic representation of pain, Pain 2(2):175–184; Joyce C R, Zutish D W, Hrubes V et al (1975) Comparison of fixed interval and visual analog scales for rating chronic pain, Eur. J. Clin. Pharmacol. 8:415–420; Downie W W, Leatham P A, Rhind V M et al (1978) Studies with pain rating scales, Ann. Rheum. Dis. 37:378–381; Melzac R and Katz J (1994), Chapter 18: Pain measurement in persons in pain in Wall P & Melzac R (eds) Textbook of Pain, Churchill Livingston pp337–351).

Category scales, as mentioned above, present the patient with a limited number of choices of descriptor words to express their current pain intensity or pain relief. Scoring is by means of assigning a number to each category. Thus, on the five-category Pain Severity (PS) scale 'no pain' is assigned a score of '0', 'a little pain' has a score of '1', 'some pain' has a score of '2', 'a lot' has a score of '3' and a score of '4' is assigned to the category of 'terrible pain'.

These numbers are of course completely arbitrary in quantity though not in rank order, and hence parametric statistics cannot be used to compare scores.

Category scales are most useful when employing non-parametric methods to examine within-patient and between-patient responses to pain treatment, and the 'Pain Intensity Difference (PID)—the numerical change in category score following administration of a pain relieving drug—is a standard pharmaceutical industry tool.

Both analog and category scales are nowadays routinely employed in pain research and therapy, including surgical recovery monitoring administered as paper-and-pencil methods. (Hutchinson P J, Laing R J, Waran V et al (2000), Assessing outcome in lumbar disc surgery using patient completed measures, Br. J. Neurosurg. 14(3):195–9; Goldstein A, Grimault P, Henriqie A et al (2000) Preventing postoperative pain by local anesthetic instillation after laparoscopic gynecologic surgery: A placebo-controlled comparison of bupivacaine and ropivacaine, Anesth. Analg. 91(2): 403–407; Milligan K R, Convery P N, Weir P, Quinn P & Connoly D (2000) The efficacy of epidural infusions of levobupivacaine with and without clonidine for postoperative pain relief in patients undergoing total hip replacement, Anesth. Analg. 91(2): 393–397; Ellis J A, Blouin R & Lockett J (1999) Patient-controlled analgesia: optimizing the experience, Clin. Nurs. Res, 8(3):283–294.)

Current computer-based technology available on the market has a number of shortfalls. A peltier-type thermal pain stimulator (Medoc Instruments, Israel) for use in pain threshold measurements is available. The thermal stimulator has an accessory device that is a VPAS-type 'mechanical slide rule,' called the Computerized Visual Analog Scale, or COVAS, which the patient employs, by moving the mechanical cursor, to indicate the degree of thermal pain the peltier thermode has evoked during an examination. The software driving this accessory is inherent to the thermode program and cannot in its present form be modified to stand alone as a patient assessment tool. The Medoc device is hardware limited, in that it administers only one PQ test (the COPAS), and only in conjunction with the sensory testing protocol, and only by employing the 'slide switch' interface. No provision exists to incorporate nurse input or to administer Mood, Pain Relief, Pain Intensity or other scales.

Another device on the market, a software program called Back Pain Monitor (BPM, Avenet, Europe) is available and is used as a comprehensive pain and disability assessment tool for back pain patients—administering questions regarding pain status to which the patient themselves responds, and questions regarding posture, mobility and performance to which a trained therapist responds. The BPM device is likewise by design and construction limited to its present purpose and takes several minutes to complete all the questionnaire forms.

Periodic delivery of paper forms of pain questionnaires are known in the art.

The current invention meets the many needs discussed above. The software and device of the current invention enables hospitals to meet JCAHO mandates for pain control documentation—introduced on Jan. 1, 2001—and additionally provide a documentation method for demonstration of treatment efficacy of use in reimbursement justification and pain therapy (including drug) research.

SUMMARY OF THE INVENTION

The Comprehensive Pain Assessment System of the present invention includes a non-contact heat beam dolorimeter and methods for objective pain tolerance assessment, as well as an automated computerized pain questionnaire (PQ) administration device and methods which capture the patient's subjective description of their pain. The heat beam dolorimeter and pain tolerance assessment methods may be used independent of the PQ administration device and methods. Alternatively, these aspects of the present invention may be used in a combined manner. The heat beam dolorimeter and pain tolerance assessment methods, as described more fully below, index abnormal states of pain tolerance associated with the chronic pain state, and can additionally index, or measure, abnormal cutaneous sensibility states such as many pain patients suffer.

The present invention fulfills the need for a non-contact, radiant heat beam dolorimeter that provides a quantitative, objective measure of the pain tolerance level, is portable and allows for automatic data acquisition. These features of the present invention allow for its use as a cost-effective diagnostic tool in the general practitioner's office, thereby allowing for earlier assessment of neurological abnormalities than is possible with currently available pain measurement devices. The present invention allows for chronic pain diagnosis, the diagnosis of subtle sensory abnormalities, and pain measurement quality assurance. The present invention is currently alone in its ability to address both the clinical and commercial needs in quantitative pain measurement.

The present invention provides a portable apparatus for determining a subject's cutaneous pain tolerance level at any site on the body. In certain preferred embodiments, the portable apparatus is a hand-held apparatus; most preferably the apparatus employs a sonar ranging sensor to automatically regulate the delivery rate of heat to a patient's skin by a heat beam dolorimeter.

The present invention provides, as one embodiment of the invention, an improved dolorimeter which comprises a non-contact heat projector, set inside a housing assembly, for delivering a radiant heat stimulus, to cause pain in the subject; a targeting device, attached to the heat source housing assembly, for accurately positioning the heat projector for stimulus delivery; a thermopile, also attached to the heat source housing assembly, for detecting movement in response to the stimulus that indicates the subject has reached the pain tolerance level; and computer connections to the non-contact heat projector, the targeting device and the thermopile allow the computer to control the output of the heat projector and the targeting device, and also allow automatic data acquisition from the thermopile as to movement by the subject, thereby allowing the invention to be operated by a single person.

In a preferred embodiment of the present invention, both the heat source and the targeting device are focused on the same point on a subject's skin to allow measurement of the temperature over time at the site of heat contact. When a subject moves in response to reaching the pain tolerance level, the heat source and targeting device will then be focused on a different point of the subject's skin, resulting in the thermopile recording a drop in temperature.

Additionally, in accordance with an embodiment of the present invention, the computer allows for interfacing between the computer and the subject, as well as between the computer and the computer operator, to allow for input by the subject and/or the operator. Moreover, in accordance with an embodiment of the present invention, the computer automatically acquires and records input from the interface between the subject and the computer, the interface between the computer and the computer operator, thereby facilitating the invention's operability by a single person.

In a preferred embodiment, the device of the current invention is a sonar-regulated Heat Beam Dolorimeter (HBD) capable of hand-held operation in a non-contact manner for the elicitation and measurement of the pain tolerance limit.

The present invention further provides for a method of determining a subject's cutaneous pain tolerance level at any site on the body.

The present invention provides, as another embodiment of the invention, a method which comprises providing a portable apparatus comprising:

a non-contact heat projector, set inside a housing assembly, for delivering a radiant heat stimulus, to cause pain in the subject; a targeting device, attached to the heat source housing assembly, for accurately positioning the heat projector for stimulus delivery; a thermopile, also attached to the heat source housing assembly, for detecting movement in response to the stimulus that indicates the subject has reached the pain tolerance level; and computer connections to the non-contact heat projector, the targeting device and the thermopile that allow the computer to control the output of the heat projector and the targeting device, and also allows automatic data acquisition from the thermopile as to movement by the subject, thereby allowing the apparatus to be operated by a single person. Additionally, in accordance with an embodiment of the present invention, the computer allows for interfacing between the computer and the subject, as well as between the computer and the computer operator, to allow for input by the subject and/or the operator. Moreover, in accordance with an embodiment of the present invention, the computer automatically acquires and records input from the interface between the subject and the computer, the interface between the computer and the computer operator, thereby facilitating the apparatus' operability by a single person.

The method of the invention further comprises initiating a stimulus of a controlled intensity from the non-contact heat projector; monitoring the time interval between initiation of the stimulus and detection by the thermopile that the subject has reached pain tolerance level, the interval, or power-time integral thereof, being a measure of pain tolerance latency at the monitoring site, and automatically acquiring and recording the pain tolerance latency measurement or data generated by the thermopile via the computer connection with the thermopile.

Moreover, in accordance with an embodiment of the present invention, the computer processes the pain tolerance latency data to obtain statistical data, which it stores. The computer may display both the pain tolerance latency data and statistical data obtained by processing the pain tolerance latency data.

In another aspect, the current invention provides a non-contact apparatus for regulating the delivery of electro-magnetic radiation to a target site, said apparatus comprising:

a non-contact emitter;

a distance sensor; and an emitter control device, wherein the delivery of electromagnetic radiation is automatically regulated as a function of target-site distance through interaction of the distance sensor and the emitter control device.

In a preferred embodiment of this aspect of the invention, the distance sensor is a sonar ranging sensor. In another preferred embodiment, the automatic regulation of the projection of electro-magnetic radiation provides a controlled effect at the target site when target-site distance changes within an effective control range. In another preferred embodiment, the electro-magnetic radiation comprises infrared radiation and the distance sensor is a non-infrared laser.

In another preferred embodiment of this aspect of the invention, the non-contact emitter is a radiant heat source, the distance sensor is a sonar-ranging sensor, and the emitter control device is a radiant heat source control device. In this embodiment, the apparatus preferably provides an automatically controlled heating rate at the target site when the target-site distance changes but remains within an effective distance range. In this embodiment, the target site is preferably a site on a subject's skin and the apparatus is a dolorimeter for determining pain tolerance, the apparatus further comprising a non-contact temperature-measuring device, wherein the apparatus is capable of being employed for determining pain tolerance without tactile stimulation of the site on the subject's skin by the apparatus or other means. Preferably, the apparatus further comprises a hand-held fixture, so that the dolorimeter is capable of being held by a dolorimeter operator.

In another aspect, the current invention is a method for regulating the delivery of heat to a target site comprising the steps of:

(a) providing a source of electromagnetic radiation effective for delivering electromagnetic radiation to a target site;

(b) delivering electro-magnetic radiation from the source to the target site;

(c) determining a target-site distance during the step of delivering electro-magnetic radiation, wherein the target-site distance is the distance between the source and the target site; and (d) automatically regulating the delivery of electro-magnetic radiation as a function of the target-site distance.

In this method, preferably the step of determining the target-site distance utilizes sonar and the step of automatically regulating the projection of heat provides a controlled effect at the target site when the target-site distance changes but remains within an effective distance range. In another preferred embodiment the step of delivering electro-magnetic radiation comprises delivering infrared radiation and the step of determining the target-site distance utilizes a non-infrared laser beam.

In another preferred embodiment the step of delivering electro-magnetic radiation comprises delivering radiant heat and the step of determining the target-site distance utilizes sonar. Preferably, said step of automatically regulating provides a controlled effect at the target site when the target-site distance changes within an effective control range. In a further preferred embodiment, the target site is a site on a subject's skin, said method further comprising determining temperature of the target site without contacting the target site, wherein said method is capable of determining pain tolerance without tactile stimulation of the site on the subject's skin. In a further preferred embodiment, the method further comprises providing an apparatus for carrying out the steps of delivering radiant heat to a target site, determining the target-site distance, automatically regulating the projection of heat, and determining the temperature of the target site. Preferably this apparatus is carried out while the dolorimeter is held by a dolorimeter operator.

In another preferred embodiment of this aspect of the invention, the non-contact emitter is a light source, the distance sensor is a sonar ranging sensor, and the emitter control device is a light source control device. Where the non-contact emitter is a light source, preferably the apparatus provides a controlled amount of energy at the target site when the distance of the light source to the target site changes but remains within an effective distance range.

In another aspect, the current invention provides methods and interface platforms effective for implementing pain monitoring methods for delivering pain questionnaires to patients at periodic, preferably regular (time settable), intervals. The methods and interface platforms may harvest analgesic drug data from nurses attending the patients, and may provide simple statistical analysis of collected data useful both at the bedside and at central base-stations. The methods and interface platforms may provide additional functions based on analysis of patient pain data. The devices and methods developed will greatly improve responsive pain therapy in pain-suffering patients and will additionally provide a centralized documentation method that will meet JCAHO guidelines.

The current invention provides a Computerized Pain Assessment Tool, called the COMPAT method or the COMPAT software herein, and hardware, called the COMPAT device herein, that runs the COMPAT software. The current invention provides a COMPAT system, also called a COMPAT patient pain management system herein, that comprises the COMPAT device running the COMPAT software as well as a data processor. The COMPAT device may include the data processor, and therefore, in certain embodiments, the COMPAT device is the COMPAT system.

The COMPAT software, COMPAT system, and COMPAT device may be used to assess a patient's subjective pain state at regular, settable, intervals following surgery or other procedure or in response to pain-relieving drugs. The COMPAT device may be a software-driven Pain Questionnaire resident on a touch-screen computer interface. In certain embodiments, it administers any, or all, of four questions to the pain patient: two visual analog (Pain and Mood) and two category scales (Pain Severity and Pain Relief). The COMPAT device may be equipped with a 'Nurse Input' screen where the caregiver can record drugs, doses and times administered, may provide for the entry of behavioral and 'vital signs' observations in addition, and a Physician Review screen, which presents a graphical history of patient and nurse annotations.

In one embodiment, the COMPAT device comprises independent low-voltage platforms at each patient's bedside capable of being manually downloaded to a nursing station or a physician office base station. In another embodiment the COMPAT device employs wired or wireless networking methods to directly link multiple units to base-stations in nurse and doctor's offices. In another embodiment, the device may be linked with PCA (Patient Controlled Analgesia) controllers to autoadminister analgesic injections. In yet another embodiment, the COMPAT device fulfills nurse call functions if pain relief is inadequate, and serves other integrated purposes within the ward patient care plan.

The current invention provides a COMPAT device and a data processor. The COMPAT system that may be considered the COMPAT device alone, when the data processing function is performed by the same microprocessor as the COMPAT software, or when two or more microprocessors that perform the two functions are used. In certain embodiments, the COMPAT system includes the population of COMPAT devices and the nursing and/or physician base stations that communicate with the COMPAT system, as well as other devices that are part of the pain management system, including PCA devices and other peripherals. Internet sites and Internet servers may also be part of the COMPAT system, if they assist in patient pain management as part of a system using the COMPAT software.

BRIEF DESCRIPTION OF THE DRAWINGS

FIG. 14 shows a Pain Severity Category Scale Screen.

FIG. 15 shows a Pain Relief Category Scale Screen.

DETAILED DESCRIPTION OF PREFERRED EMBODIMENTS

Figure 1A:
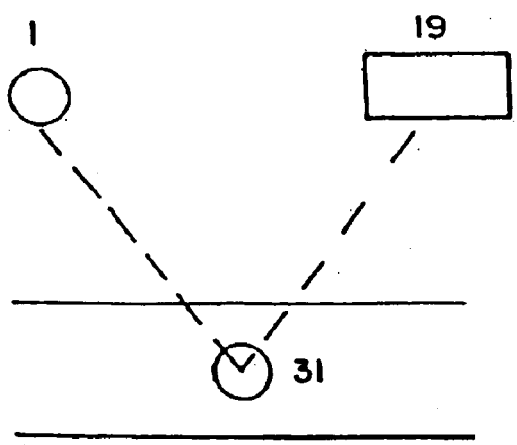
FIGS. 1A and 1B are illustrations of the operation of the dolorimeter.
Figure 1B:
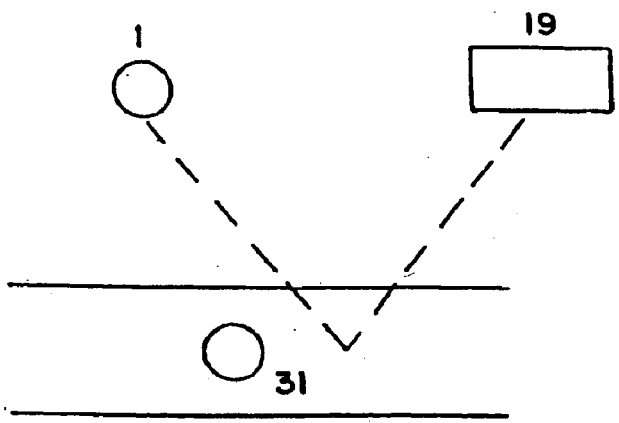

Referring to FIGS. 1A–1B there is illustrated a method for determining a subject's cutaneous pain tolerance level at any site on the body. As illustrated in FIG. 1A a heat source 1 and a thermopile 19 are focused on the same site of a subject's skin 31 where the pain tolerance level is to be measured. The thermopile 19 continually measures the increase in skin temperature caused by the heat source 1 at that site on the subject's skin 31.

Figure 2:
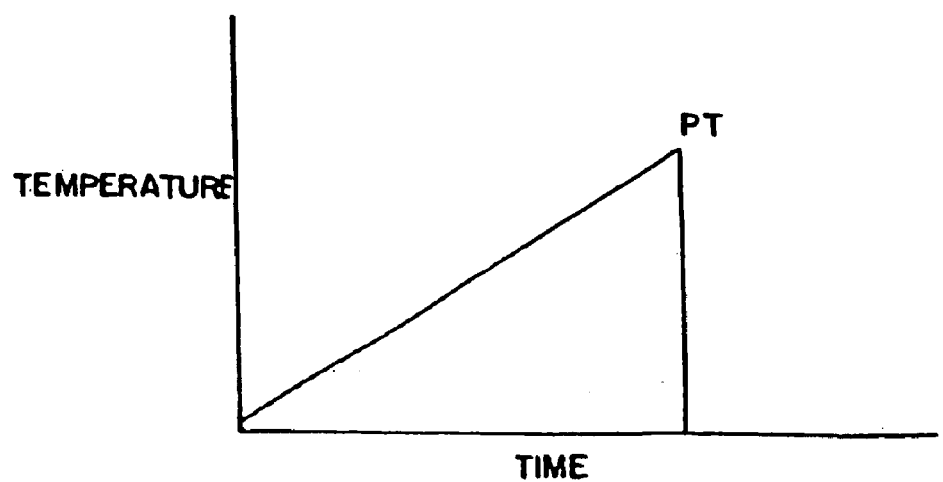
FIG. 2 is a representative graph recording the change in temperature over time measured by the targeting device of the dolorimeter.

Upon reaching the pain tolerance level (PT), the subject moves and thereby the site that the heat source 1 and thermopile 19 are focused upon changes (FIG. 1A) to a previously unheated site. As a result of reaching the pain tolerance level (PT), the thermopile records a sharp drop in temperature at the site of focus, as illustrated in FIG. 2. In a preferred embodiment, the thermopile comprises an infrared-sensing thermopile, such as an Omega OP65 device.

Figure 3:
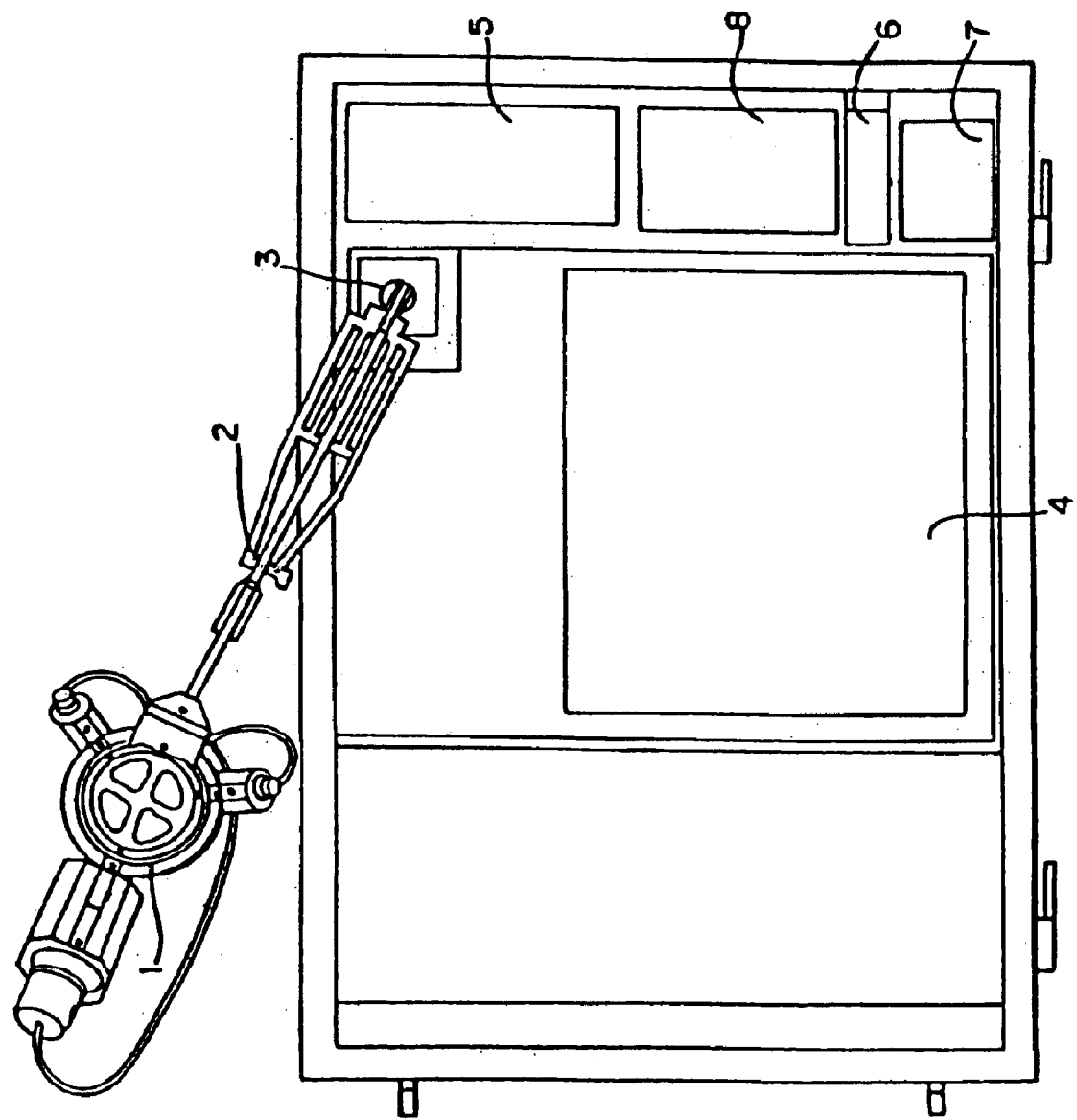
FIG. 3 is a generalized block diagram illustration of a top view of the dolorimeter instrument package in accordance with a preferred embodiment of the invention.

Referring now to FIG. 3, there is illustrated a portable apparatus for determining a subject's cutaneous pain tolerance level at any site on the body in accordance with a preferred embodiment of the invention. The apparatus comprises a heating head 1 associated with a double linkage parallelogram arm 2, preferably fabricated out of hollow steel tubing. The linkage arm is further connected to a pivot base 3, which is present in the dolorimeter instrument package. The dolorimeter instrument package is encased in a portable container and comprises, in addition to the pivot base, a lap top computer 4, such as an IBM 760C portable computer, which receives electrical power from an internal battery. The computer has two PCMCIA card slots, and one of the slots contains an interface card, such as a ComputerBoards PCM-DAS 16/12D interface card. This card contains four digital inputs, 8 differential analog-to-digital input channels and four digital outputs. The internal computer battery inputs its voltage status to the computer via a differential analog-to-digital input channel. Associated with the computer in the dolorimeter instrument package is a battery 5 to provide electrical power to the components of the heat beam dolorimeter, an electrical strip 6, a battery charger 7 for recharging the heat beam dolorimeter battery and the computer battery, and a lap top computer power supply 8.

Figure 5:
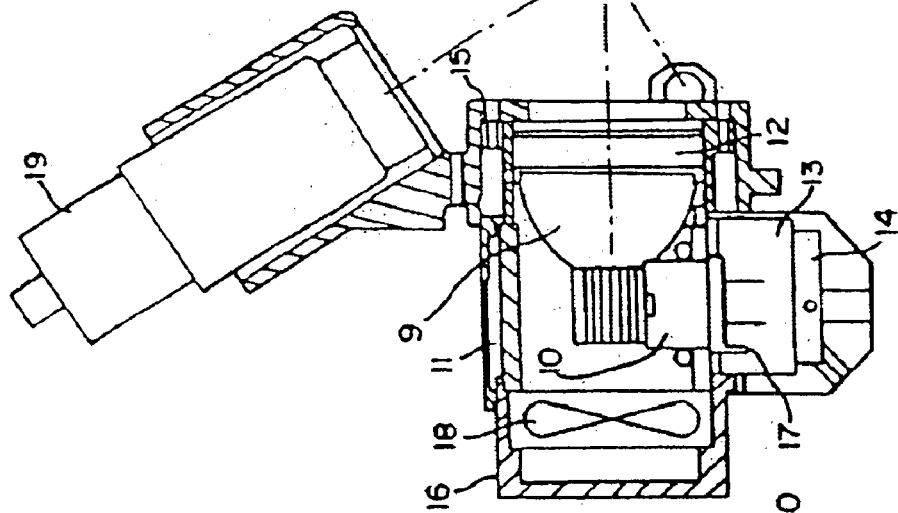
FIG. 5 is a top view of an assembled dolorimeter heating assembly in accordance with a preferred embodiment of the invention.
Figure 4:
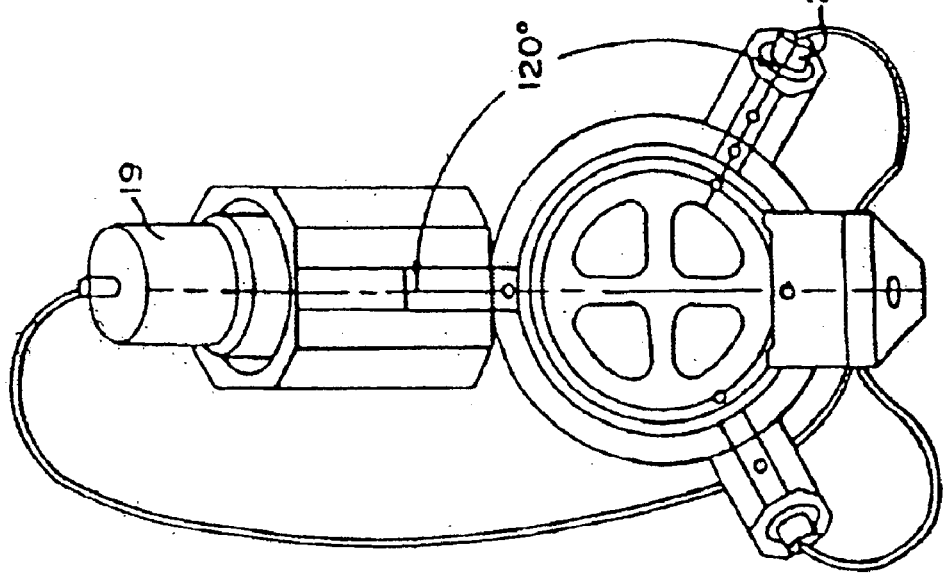
FIG. 4 is a side view of an assembled dolorimeter heating assembly in accordance with a preferred embodiment of the invention.

Reference is now made to FIGS. 4–5, the heat beam dolorimeter comprises a heat projector 9, such as a Sylvania type DNE 150 watt, 24 volt, tungsten-halogen projector lamp, which gives approximately concentric radiance as measured by the naked eye when viewing the projected light on a screen 18 centimeters from the bulb. Other bulbs can be used having the same or similar projected radiance pattern and power-temperature profile, provided the bulb is first calibrated. The preferred calibration criteria are that the bulb must create (i) a broad focal spot size of peak heat delivery of 20+/−0.2 mm at 5.08 centimeters from the edge of the lamp housing, measured using Sharp FO-20PrW thermal paper over 20 seconds exposure; and (ii) a temperature rise of 5.2+/−0.1 centigrade degrees at the calibrating thermocouple at the tenth second of irradiation. Of course, other similar calibration criteria meeting these generally preferred characteristics can be used if desired.

The heat projector 9 is set in a lamp socket 10 inside a heat source housing assembly comprising a heat source cover 11, a stove 12, a carriage trap 13, a bottom cover 14, a front aperture cover 15, a back cover 16, and a carriage 17. The heat source housing assembly is preferably constructed of 2024 aluminum for optimal heat dissipation, except for the front aperture cover 15 of the housing, which is preferably milled from 1045 steel. Associated with the heat projector is a miniature cooling fan 18 within the posterior of the heat projector housing assembly. Also associated with the heat projector is an infrared sensing thermopile 19, such as an Omega OP65 device. The thermopile 19 receives electrical power from the battery 5 in the dolorimeter instrument package. Also associated with the heat projector are two laser positioning diodes 20 with integrated optics and driver, such as those made by Coherent Applied Laser Systems, part number 0220-058-00, with output power of 4.2 mW and an emission wavelength at 670 nM (visible, red). The laser positioning diodes 20 of the targeting device 19 receive electrical power from the battery 5 in the dolorimeter instrument package. The two positioning diodes 20 and the thermopile 19 are mounted 120 degrees from each other on the exterior of the heat projector housing.

Figure 8:
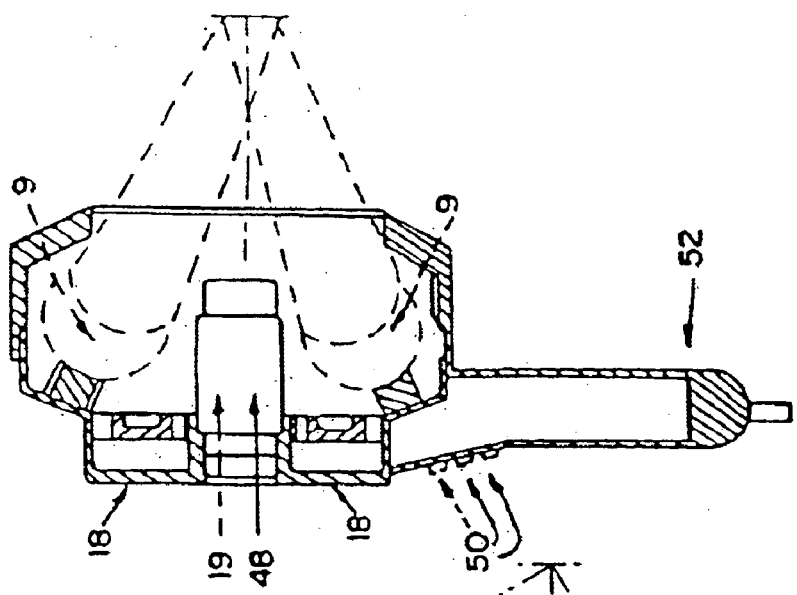
FIG. 8 is a section view of an assembled dolorimeter heating assembly in accordance with a preferred embodiment of the invention.

In a preferred embodiment of the invention as shown in FIG. 8, a hand held fixture is utilized to hold the heat source housing assembly. The hand held fixture can be made of any lightweight material including but not limited to aluminum and plastic. The hand held embodiment includes two projector bulbs 9 to generate the heat beam, and provide even illumination of all parts of the monitoring site. The thermopile 19 is positioned between the projector bulbs. Cooling fans 18 are located behind each projector bulb. The hand held unit incorporates thumb controls 50 onto a handle 52 for ease of operation. A commercial laser diode-based distance-measuring device 48 is also located between the projector bulbs. Preferred commercial laser distance-measuring devices include, but are not limited to a Keyence LB-11 sensor head and LB-70 controller (Keyence, Schaumburg, Ill.). The laser distance measuring device provides a display indicator to tell the operator how to adjust the hand held unit (i.e., toward or away from the skin), in order to keep it at the proper distance, and also provides a feedback signal by which the projector intensity can be increased or decreased automatically to compensate for small discrepancies in distance not controlled by the operator. The noncontact heat projectors, the thermopile and the laser distance-measuring device are all focused on the monitoring site on the subject's skin. Of course, a dedicated electronic control system can be utilized as the processing means, in place of the IBM 760 portable computer and the computerBoards PCM-DAS 16/12D interface card.

Figure 6:
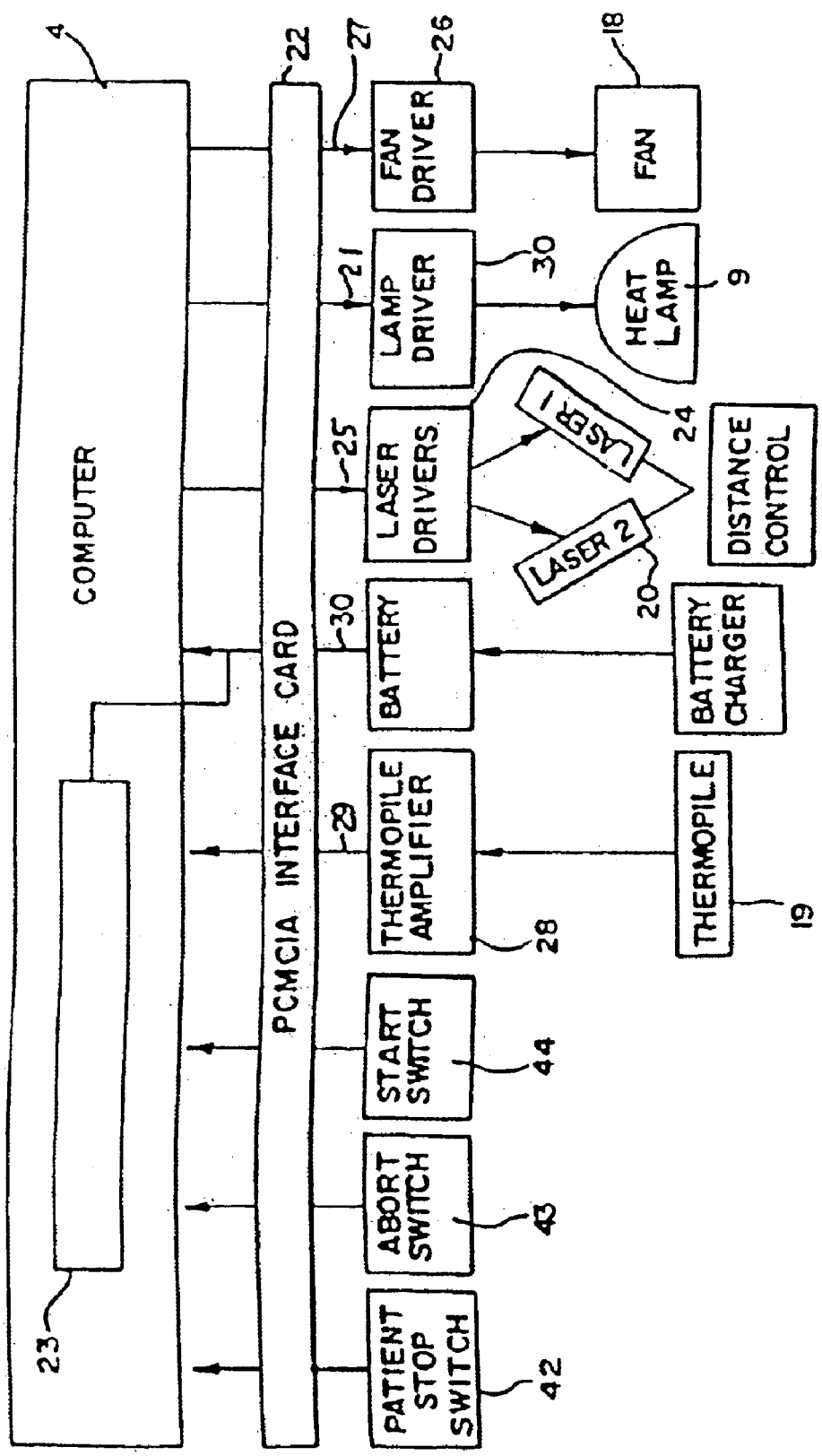
FIG. 6 is a block diagram of the computer connections with the dolorimeter apparatus in accordance with a preferred embodiment of the invention.

Referring now to FIG. 6, the heat projector 9 is controlled by a digital output connection 21, through the PCMCIA interface card 22 with the computer 4. The digital output controlling the heat projector 9 has the capability of pulse frequency modulation. By having this digital output drive a one shot circuit, the pulse frequency is changed to pulse width modulation. This pulse width modulation is used to control the intensity of the heat beam. The computer determines the width of the pulse driving the heat projector using a calculation based on desired heat projector intensity and the battery voltage reading 23. As the battery is discharged, its voltage decreases and without some compensation, the heat projector intensity would also decrease. For this reason, the computer preferably modifies the pulse width to compensate for the measured battery voltage.

The two laser positioning diodes 20 are connected to laser drivers 24 that are controlled by the computer 4 via a digital output connection 25 through the PCMCIA interface card 22. The miniature cooling fan 18 is connected to a fan driver 26 that is controlled by the computer 4 via a digital output connection 27 through the PCMCIA interface card 22. The infrared-sensing thermopile 19 is connected to an amplifier 28 delivering a signal which is related to the skin temperature target but not necessarily calibrated to read exact temperature. When the temperature measured by the thermopile 19 drops significantly, as occurs when the patient moves at their pain tolerance point, the heat projector 9 disengages and reports the time—the tolerance latency—to the database via a differential analog-to-digital input channel 29, through the PCMCIA interface card 22. The battery which powers the heat projector 9 also communicates to the computer via a differential analog-to-digital input channel 30 through the PCMCIA interface card 22.

Figure 7:
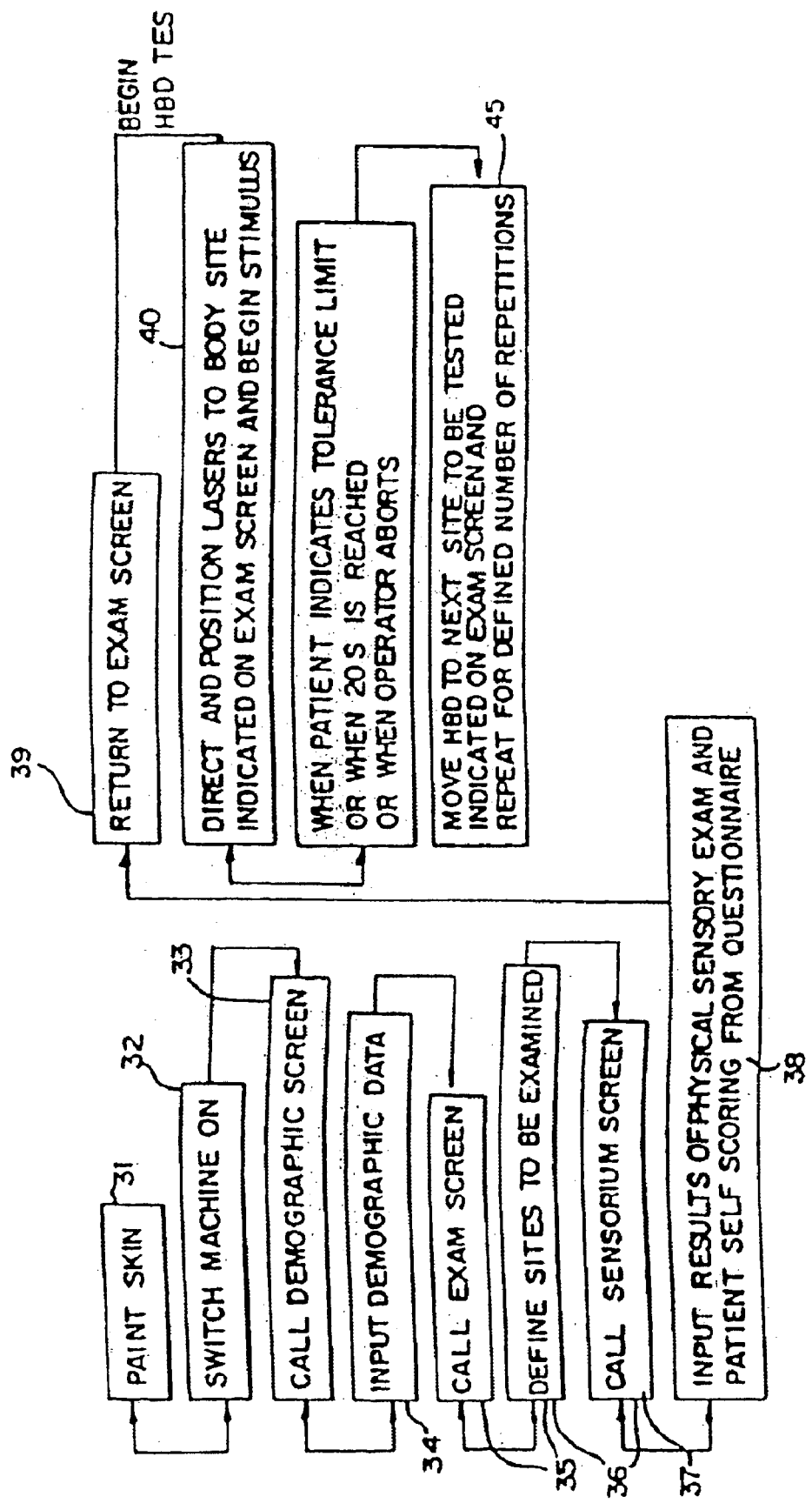
FIG. 7 is a flow chart detailing a method for determining a subject's cutaneous pain tolerance level at any site on the body in accordance with a preferred embodiment of the invention.

Referring now to FIG. 7, there is illustrated a method for determining a subject's cutaneous pain tolerance level at any site on the body in accordance with a preferred embodiment of the invention. The method comprises providing a portable, computerized heat beam dolorimeter apparatus as disclosed above. An embodiment of the method comprises painting the subject's skin 31 at the site to be tested with a matt black skin stain, such as Avery-Dennison type 42 non-toxic ink, to enhance absorption of the radiant heat generated by the heat projector.

In a preferred embodiment, the computer software was written in Microsoft Visual Basic, running under Windows 95. Of course, other language and operation systems can be used if desired. Each screen (called a "Form") is provided with "buttons" to operate choices. The buttons are selected by the mouse on the computer. When the computer powers up 32 the first form displayed is called the MainHeat Form. This form provides selections to either calibrate the dolorimeter apparatus or to input demographic data for the experiment. The calibration form allows the operator to record the temperature caused by the heat beam when focused on a temperature sensing device. The demographics screen 33 has text boxes for entry of relevant demographic data 34 concerning the subject. From the demographics form one can press a button to go to either the therapeutic exam setup form 35, for use when the subject is to be tested both before and after some type of therapy, or the standard exam setup form 35, which presents an outline of the subject's body with sites to be tested designated as such 36. This information is processed to the standard exam setup form, and the data is automatically entered into a table in the sensorium form 37, where the technician also inputs data from the subject's pain questionnaire 38. The recorded data is then archived to the database.

To measure tolerance latency at a particular site, the exam form 39 is recalled on the computer, and the heat beam dolorimeter head is pointed at the approximate body site on the subject and the start button 44 on the computer is depressed one time. The two laser diodes then illuminate and the dolorimeter head is adjusted so that the two laser beams converge at the center of the black spot on the subject's skin. The start button 44 is depressed a second time and the lasers extinguish while the heat beam initiates 40. The heat beam stimulus is stopped, and the "beam on" time recorded, either when the patient moves, as detected by the infrared sensing thermopile, or when the subject presses the patient stop button 42. A third button, the abort button 43, is pressed by the operator when some distracting event occurs in the room which could invalidate the reading. Referring to FIG. 6, the status of the stop 42, abort 43 and start buttons 44 are all communicated to the computer via a digital input connection through the PCMCIA interface card.

From the exam form, means are provided on the screen for going to the sensorium form where the data may be viewed to verify completeness before permanently saving it. From that screen, the operator may return to the demographics form and process another subject, or may test the next site indicated on the exam screen 45.

Figure 9A:
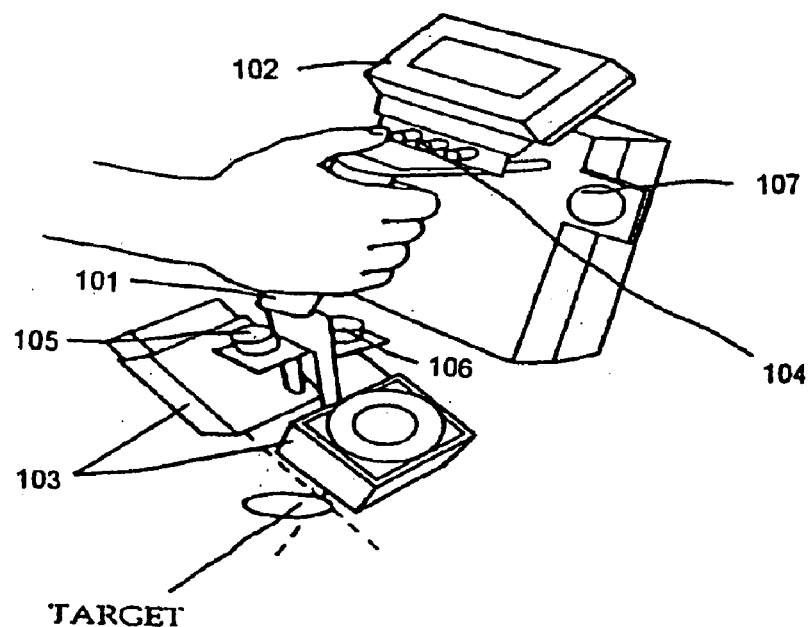
FIGS. 9A and 9B illustrate the hand-held component of the sonar-controlled dolorimeter, FIG. 9B showing detail of one of the two EMR emitters of a preferred embodiment.

Referring now to FIG. 9A, a preferred embodiment of the invention is a device, called a sonar-controlled heatbeam dolorimeter (sonar-controlled HBD), for the measurement of pain tolerance using a sonar distance-measuring apparatus. This preferred embodiment employs twin focused beam radiators directed at the skin target and a sonar range-finding device to constantly and accurately monitor the distance to the skin target. As this distance varies within limits due to natural involuntary movement of the operator holding the device, the power supply to the emitters is automatically altered by this invention so as to counter the effect of such movement on the energy delivered to the skin target, thus obviating the effect of such movement on stimulus temperature rate and maintaining this substantially constant at the desired incident intensity.

The sonar-controlled HBD device is employed in sensory testing of the subject. Sites to be tested and tolerance latencies measured can be rendered more reproducible if first painted with a special matt-black paint formulated with iron oxide and binders that do not form a palpable film on the skin, such that, when dry, the paint does not stimulate the mechanoceptive touch receptors of the skin. Typically the sites to be tested include the hands, arms, feet and/or chest of the subject; of course, the sites can be tested if desired (see: Lipman, Blumenkopf and Parris, 'Chronic pain assessment using heatbeam dolorimetry' Pain 30:59–67 (1987)). The subject to be tested is instructed in the sensory continuum of the pain sensibility range and instructed not to respond by movement until the 'pain tolerance limit' is reached. This is an unmistakable end-point with the HBD, a sudden and brisk sensation of unendurable pain resulting in movement of the instructed subject. The HBD is then directed to each body site in turn and the patients movement at each test-site recorded automatically by the device's non-contact temperature measuring device, (e.g., a thermopile,) which records the cumulative thermal energy and exposure time required to reach the end-point at each site. The sites are tested multiple times, typically five (Lipman et al, 1987), as described above and the associated computer calculates various statistics characterizing the examination.

Figure 9B:
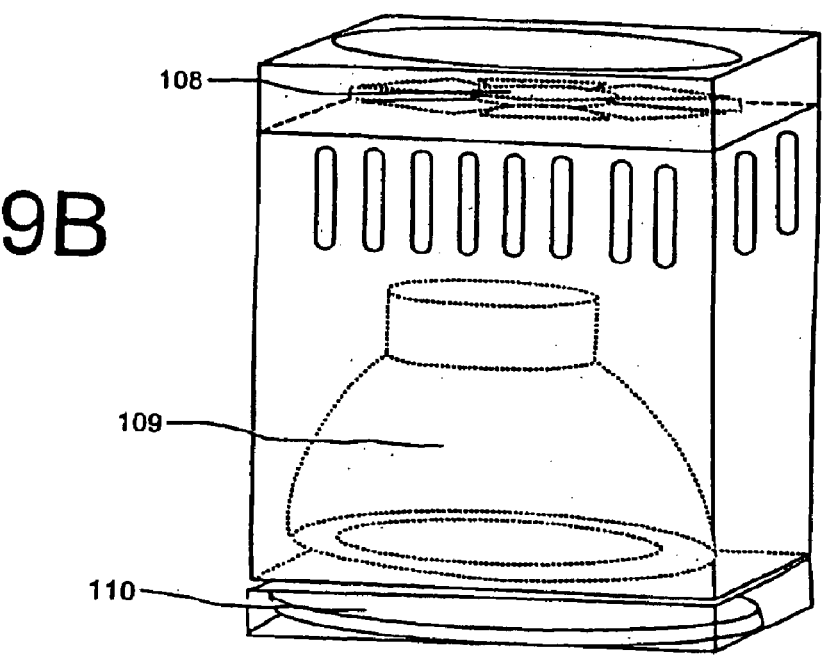
Figure 10:
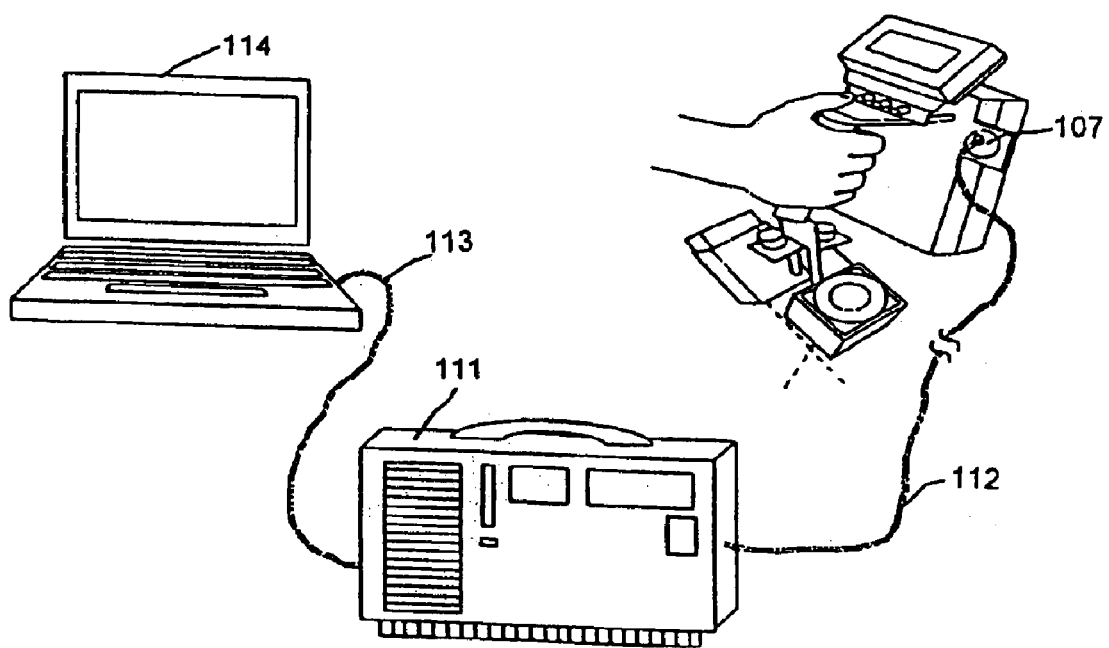
FIG. 10 is illustrates the connection of the components of the device of FIG. 9A.

The heatbeam dolorimeter device employs a pulse width modulated (PWM) variable power supply (20, in FIG. 11) capable of rapidly varying the intensity of the radiant heat of the emitters within certain limits, and with precision, under software control. The preferred hand-held sonar HBD hand-held device (FIG. 9A) is attached, as shown in FIG. 10, to a power and control circuitry in the control unit 111 by a flexible umbilicus 112 which is connected to the hand-held portion of the device via a multipin amphenol connector 107 and operated by pressing the appropriate control buttons 104. The hand-held sonar HBD employs as emitters two—and, optionally, more than two—infra-red projectors of heat and light (103 in FIGS. 9A and 9B), that are cooled by electrical fans 108 and geometrically arranged in the hand-held mechanical frame or support 101 on which they are mounted so that the region of overlapping intersection of their beams falls at the target site on the skin in an ellipse of the appropriate size and shape suitable for tolerance limit heatbeam dolorimetry. This elliptical target size preferably has a major axis of about 2+0.3 inches and more preferably about 1+0.1 inch; of course, other sized target areas could be used if desired. These emitters 103 may employ projector lamps 109, such as, for example, these manufactured by WICO (Niles, Ill.), type ENH. Other types of heat or light or other EMR projectors may be used, provided they meet requirements for energy delivery type, rate and effective control range. A sapphire lens 10 or other lens particularly offering low resistance to EMR transmission is mounted at the outlet of the two projectors. The hand-held device employs an electronic range-finding sensor 105, which can be either sonar or laser, the preferred embodiment using sonar, capable of measuring the distance to the skin target site with great precision (e.g., 0.01 inch or better) and of refreshing this measurement at high frequency (settable, 0.1 Hz or faster). A non-limiting example of a suitable ultrasonic sonar sensor in the operating range of 4 to 40 inches and with a sample frequency of 0.1 Hz, is the M-5000 ultrasonic sensor with 0.25 mm (0.010 inch) precision, manufactured by Massa Instruments (Hingham, Mass.), employed in the preferred embodiment. As exemplified in FIG. 11, the sonar sensor 105 fulfils two functions: First, it provides feedback signals to the sonar controller 118, which can then signal the liquid crystal display (LCD, 102) or any other suitable visual interface, to direct the operator in placing the HBD device at the approximately appropriate distance (at the midpoint of the effective control range as defined by look-up table FIG. 12) from the skin; and secondly, by means of the power control circuit 120 in the control unit 111 it provides feedback which controls the power output of the infra-red projectors 3. Thus, within the region of beam coincidence and within the region of sensor operation, which common envelopes are typically the effective control range, the hand-held HBD auto-regulates heat delivery in response to distance changes, to maintain the incident radiation delivered to the target at an "ideal" and substantially constant rate, substantially equivalent, preferably statistically equivalent, to that which would be delivered had the device been stationary. In addition, the device employs a non-contact optical thermopile (thermocouple) sensor 6, such as an Exergen (Watertown, Mass.) Irt/c type, to measure infrared emissivity of the skin at the target site; the associated computer software records these measurements during the course of the assessment at a settable frequency, preferably of no less than 0.1 Hz.

Figure 11:
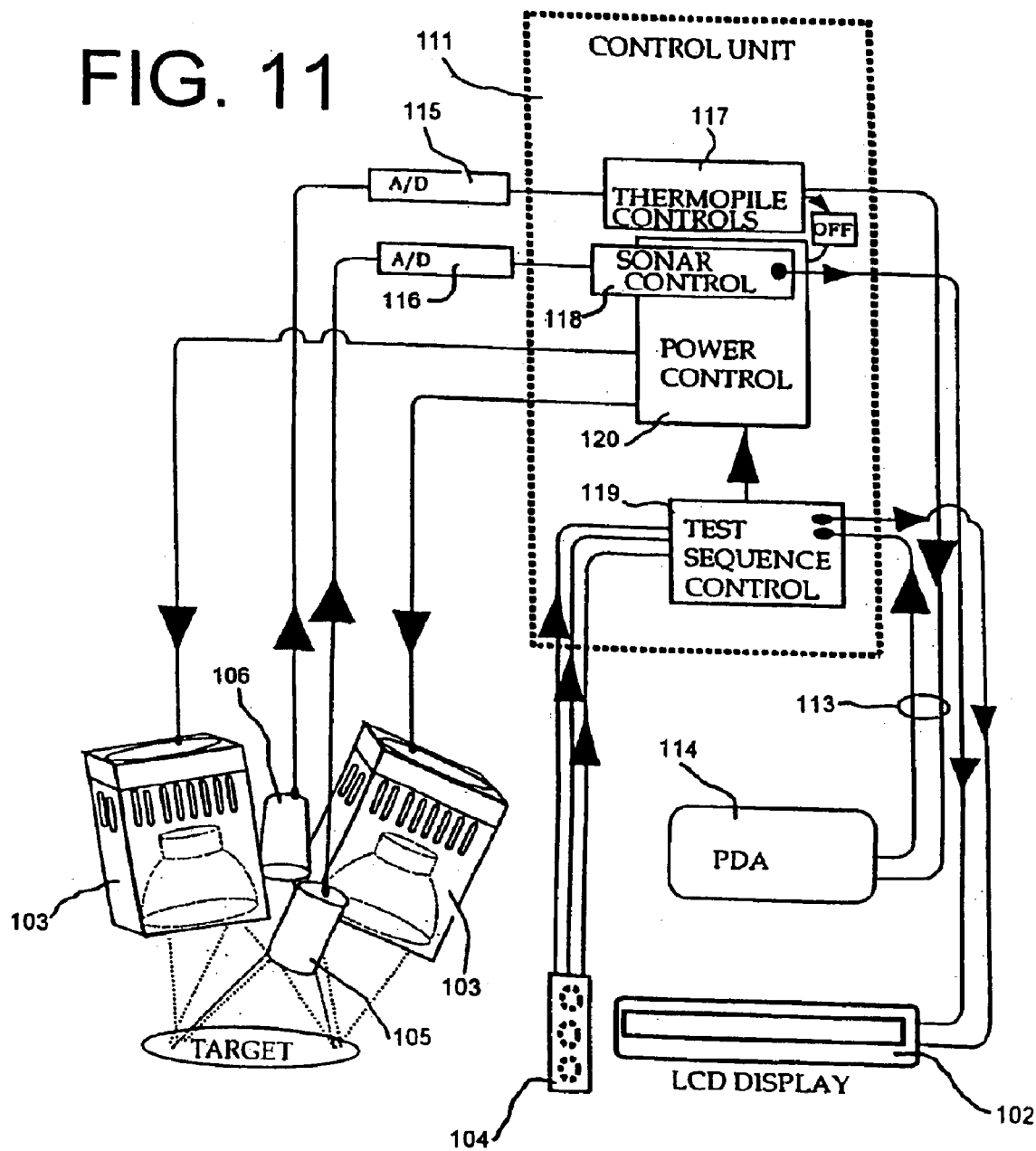
FIG. 11 illustrates the power and electronic information flow diagram of the device of FIG. 9A.

The connection of the components of the Sonar HBD are shown in FIG. 10 and FIG. 11. The power control unit 111, is connected at a connection site 107 to the hand-held HBD unit by a flexible umbilicus 112, which in a preferred embodiment is Alpha (Sunbury-on-Thames, Middlesex, England) 9-pair 22 AWG foil shielded wire. In certain embodiments, power flows to the emitters through the umbilicus 112 as regulated by the power control 120. In certain embodiments, command signals to the control unit 111 are sent from the operator's push buttons 104 through the flexible umbilicus 112 In certain embodiments, distance data flow from the sonar ranging mechanism originating in the signal from the sonar sensor 105 are sent to the sonar control unit 118 through the flexible umbilicus 112. The operator initiates the test procedure and stores input data regarding the identity of the patient and related information at the hand-held computer interface 114 which may be, for example, a PDA (personal digital assistant) or HPC (handheld personal computer), or other interface, connected to the Control Unit 111 by a serial cable 113 through which sonar and thermopile data flow from the thermopile 117 and sonar 118 control circuits. The computer interface 114 may include commercially available database software for storing test data from the control unit 111 corresponding to the patient. The computer 114 can also include a conventional serial port for receiving data over the serial cable 113, as well as a standard operating system, such as Windows CE or Windows 98 from Microsoft, that provides application programming interfaces (APIs) that allow data from the serial port to be read by the database software.

The power and control information flow of the invention is diagrammatically illustrated in FIG. 11 Following data input to the hand-held computer 114 by the operator, and following sequence initiation by the operator pushing the appropriate button 104, the test sequence logic control 119 of the control unit 111 then directs the operator to test a particular part of the body, placing this instruction on the LCD display 102. After the operator acknowledges readiness by pushing the appropriate control button 104, sonar signals from the sonar sensor 105, having been digitized by the analog to digital converter 118, are then used to control the LCD display output 102 and to guide the operator in manually positioning the device correctly. When correctly positioned according to the information displayed on the LCD, the operator pushes the appropriate button 104 to initiate the test stimulus, and the power control circuit 120, energizes the emitters 103 and automatically controls—increases or decreases, as appropriate—the power delivered to the emitters in response to sonar feedback 118 detected within the sonar circuits affiliated with the power control circuits 120. Both thermopile and sonar signals having been locally processed in the hand-held unit by the analog to digital converters (A/D) 115, 116 and their digitized signals passed respectively to the thermopile control 117 and sonar control 118 circuits. When the subjects pain tolerance limit has been reached (i.e., they reflexively withdraw from the stimulus), the thermopile control circuits 117 detect this large change in site-emissivity monitored by the thermopile sensor 106 and signal the power controls 120 to stop emission. The test sequence logic controller 119 then directs the operator to move to the next body site to be tested, displaying this information on the LCD display 102, and the test procedure continues and is repeated at the next site to be tested.

The functionality of the control unit 111 described above in connection with FIG. 11 can be implemented using one or more software programmable controllers (not shown), such as commercially available microprocessors, microcontrollers, or the like. In this embodiment, the controller can be coupled to a memory using a conventional bus. The memory can store one or more software programs for directing the control unit 111 to perform the functions, including the function of the thermopile controls 117, the sonar control 118, the power control 120, and the test sequence control 119, as described herein. The controller can also execute a software routine for interfacing the LCD 102 to the test sequence logic control 119 and the sonar signals.

Figure 12:
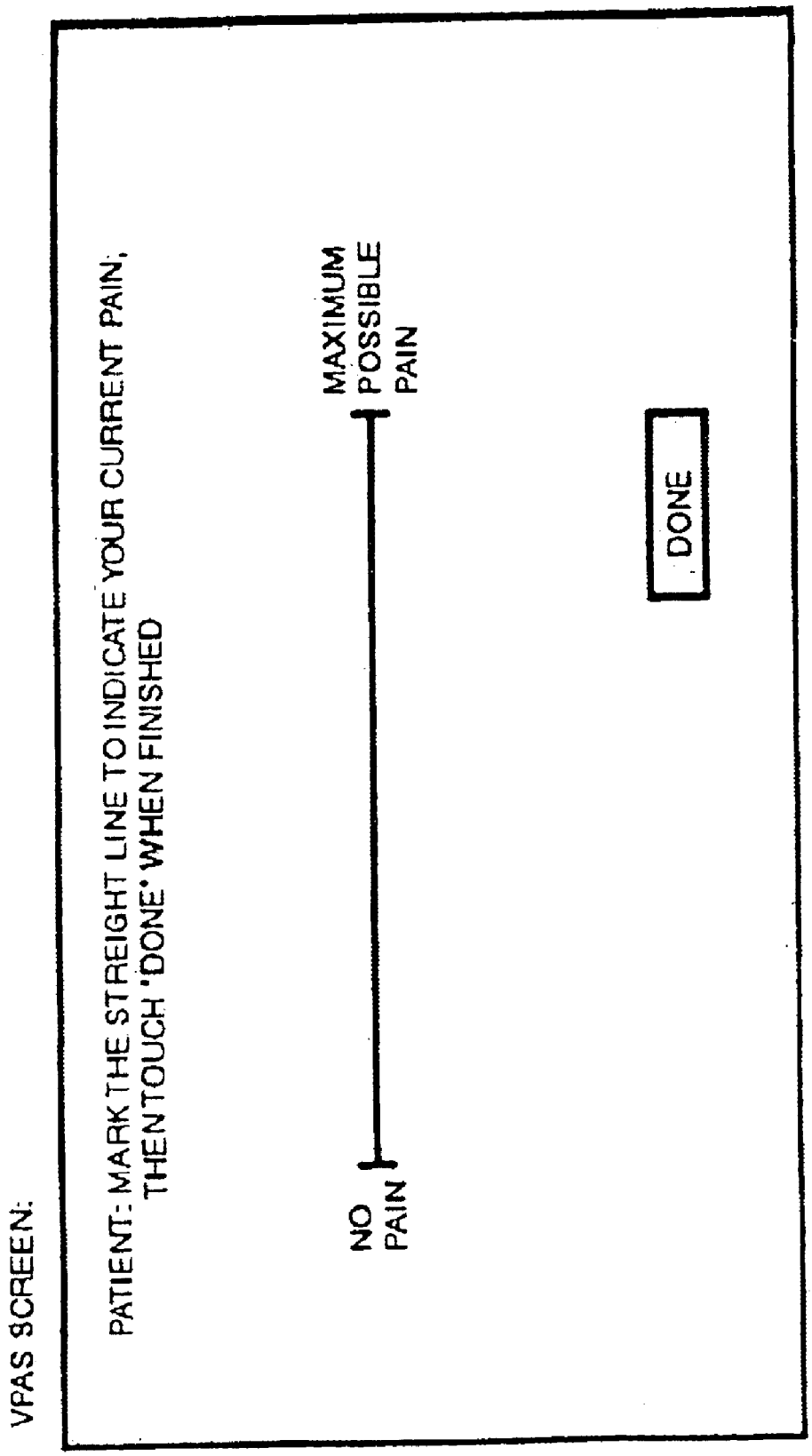
FIG. 12 shows a Visual Pain Analog Scale screen.

The sonar control may include a software routine, executable by the controller, for regulating the power output of the emitters 103. The software may, for example, regulate the power output of the emitters 103 by utilizing a stored look-up table that contains pre-determined offset values. An example of logic of the sonar feedback procedure which may operate on the look-up table software procedure is illustrated in FIG. 12. Represented in the figure is an example of a process whereby sonar signals are compared with software-stored norms representing the "nominal" or optimal operating distance. If this comparison indicates that the device is indeed held at the optimal (or "nominal")

distance, typically no change in emitter power occurs. If, however, an offset is detected, either positive or negative, the software may route the offset signal to a location in the look-up table corresponding to that specific offset distance (−5 to +5, in the distance parameter table of FIG. 12), triggering an instantaneous change in power offset compensation value (+5 to −5, in the power parameter table of FIG. 12), corresponding to the distance offset value. This power offset in turn modifies the power control (i.e., pulse width modulation) of the emitter and the energy transmitted therefrom. Thus, the closer that the sonar detects the target, the less power is applied to the emitter, and, conversely, the greater the distance detected by the sonar, the greater is the power applied to the emitter. Values of distance corresponding to the eleven steps from −5 to +5 may be empirically determined by an optical bench procedure (see below), and power offset values (−5 to +5) may be determined by a trial-and-error procedure during device calibration. For simplicity and illustration only, the example and the figure describes a sonar-controlled feedback procedure employing eleven distance/power steps; of course other number of steps are possible depending on the effective control range and the characteristics of sensor type, power controls, and emitter type. In another embodiment, the software may, for example, regulate the power output of the emitters 3 by means of a continuous solution of an equation for a distance, maintaining power at a desired level in response to varying distances.

In another aspect not limited to HBD technologies, the present invention is a non-contact apparatus for regulating delivery of electro-magnetic radiation (EMR). "Electromagnetic radiation" refers to the radiated energy field emitted by the passage of electrons through a material conductor, such as a lamp filament, and may span the EMR spectrum from gamma rays, X-rays, visible light-, infra red through ultra-violet and microwave radiation. An "apparatus for regulating delivery of EMR" refers to an apparatus that generates, propagates, and directs a beam of EMR at a target and regulates the intensity of radiation incident upon the target, including regulation in response to movement of the target. Preferably, incident radiation intensity is maintained substantially constant at the target, most preferably constant, regardless of distance within an effective control range. Examples of such apparatuses include, but are not limited to, radiant heat projecting devices including heatbeam dolorimeters, warming lamps, (e.g., warming lamps used in pediatric care), paint-drying and enamel-baking heat radiators, radiators for target incineration and surface etching, and the like; ultraviolet projecting devices for curing plastics, for setting EPROM devices, for tanning purposes, for use in psoralen or other photoreactive therapies, for fingerprint visualization, and the like; X-ray devices for medical imaging, metal fracture examination, and similar applications, laser projectors for cutting, etching, and curing purposes, visible light devices for film processing, for photoreactive chemistry and for optical and optoelectronic signaling purposes, where incident radiation intensity delivered to the target must be automatically regulated as the emitter target distance may change. "Automatic regulation" refers to the completely autonomous regulation by circuitry and/or a computer program of the emitter control means in response to signals received from the distance sensor.

As in the HBD technologies described above, this aspect of the invention employs laser or sonar (a sensing method) to measure distance between a target and a non-contact emitter. A "non contact emitter" refers to the emitter or source of EMR, which does not physically touch the target being irradiated. It may be a radiant projector of heat or light or EMR of any wavelength. Typically, it is a visible light photographic film-type projector lamp, an infra-red emitter, or an ultraviolet projector or, in certain applications, an X-ray lamp. "Emitter control device" refers to the means of powering the emitter at a particular and desired intensity, including—in the case of the present invention—a means of overcoming and neutralizing the effect of changes in distance between emitter and target. This may be achieved, for example, by a variable positioning mechanism such as a motor drive or a variable and regulated power supply of a stationary emitter, or both. Preferably the emitter control device is capable of rapidly changing (i.e., one hundred milliseconds or faster) the emission intensity incident at the target from one value to another value in response to a control signal provided by the control circuits and/or computer software in response to signals from the distance sensor. "Distance sensor" refers to a device for measuring the spatial separation of target and emitter, in certain preferred embodiments, without physically touching the target. It may employ sonar, laser, or other non-contact means. For use with emitters not projecting infra-red radiation, a laser range-finding sensor operating in the infra-red range may be employed, such as a Keyence model LB-11/LB-70 displacement sensor/controller (Keyence Corporation, Seattle, Wash.). "Sonar ranging sensor" refers to a distance measuring device which by transmission and reception of ultrasonic pulses is capable of measuring the distance between two objects, stationary or moving.

The distance-registering non-contact sensor takes distance measurements at regular and small increments of time (e.g., milliseconds or other adjustable increment) and automatically signals the EMR source control circuitry to vary either the position or the power output of the EMR source (as appropriate) in order to ensure that any change in distance is compensated rapidly and automatically. A remote, non-contact sensor takes measurements ("readings") of emitted radiation from the target during the period of EMR radiation, and these readings are recorded by an associated computer in a database. Further, should the emitted radiation sensor register a reading outside of preset limits, indicating that the target is no longer at the target site, the computer monitoring the readings may notify the EMR source control circuitry to switch off. A preferred example of this aspect of the invention related to sonar control of EMR is the hand-held, sonar-controlled HBD described above.

Preferably, the non-contact apparatus for providing regulated delivery of EMR to a target site provides a controlled effect at a target site when the target-site distance changes within an effective control range. "Controlled effect" refers to the regulation, preferably precise regulation, of incident radiation at the target according to a desired profile of energy delivery, which may be substantially constant, constant, or variable as required by the specific application. The controlled effect may be a controlled energy rate or a controlled heating. "Controlled energy rate" refers to the controlled effect where this is employed in an application that delivers EMR which may be other than heat-generating energy. "Controlled heating rate" refers to the controlled effect of EMR where this is employed in an application that delivers heat. For the sonar-controlled HBD in normal use this may be set at 1.93° C./Sec and may be adjusted to other values. "Effective control range" refers to the distance over which target irradiation can be effectively controlled within desired parameters by accurately yoking the emitter control to the distance sensor response, and is a function of the limitations of both distance sensor and the emitter. For example, for the sonar-controlled heatbeam dolorimeter this may be a range of less than about six inches. In one preferred embodiment the range is two inches (one inch further than and one inch nearer than the optimal target distance). For other applications and emitter—sensor pairs this could be very much greater (for paint drying purposes, for tanning or for incineration) or very much shorter (for UV curing of dental resins, plastics and like applications).

"Emitter control device" refers to the means of powering the emitter at a particular and desired intensity, including— in the case of the present invention—a means of overcoming and neutralizing changes in distance between emitter and target. This may be achieved, for example, by a variable positioning mechanism such as a motor drive or a variable and regulated power supply of a stationary emitter, or both. Preferably the emitter control device is capable of rapidly changing (i.e., one hundred milliseconds or faster) the emission intensity incident at the target from one value to another different value in response to a control signal provided by the control circuits and computer software in response to signals from the distance sensor.

Preferred embodiments of an apparatus for regulating delivery of EMR to a target site use a non-contact temperature measuring device, as employed in the HBD inventions described above. A "non-contact temperature measuring device" refers to a thermocouple, thermopile, infrared or other direct or indirect thermal radiation sensing device capable of measuring the temperature of a target without making physical contact with the target, for example, by quantifying infra-red radiation emitted by that target.

In another aspect, the current invention provides a computer pain assessment software tool (COMPAT). In yet another aspect, the current invention provides a stand-alone bedside device for performing the COMPAT functions. The present invention also provides a COMPAT pain management system that includes the COMPAT device and a data processor. In certain embodiments the device has remote connectivity to remote base stations by, for example, but not limited to, (1) network connection to central nurse's station and doctor's office, and/or (2) modem and/or Internet link for remote use. The device may also have additional software effector functions to fulfill patient monitoring needs in addition to pain assessment.

The current invention provides an automated pain monitoring method, the COMPAT method, that delivers pain questionnaires to patients at periodic, preferably regular (time settable) intervals. The method additionally may harvest analgesic drug administration and other data from nurses attending the patients, and may provide simple statistical analysis of collected data useful both at the bedside and at central base-stations.

Figure 13:
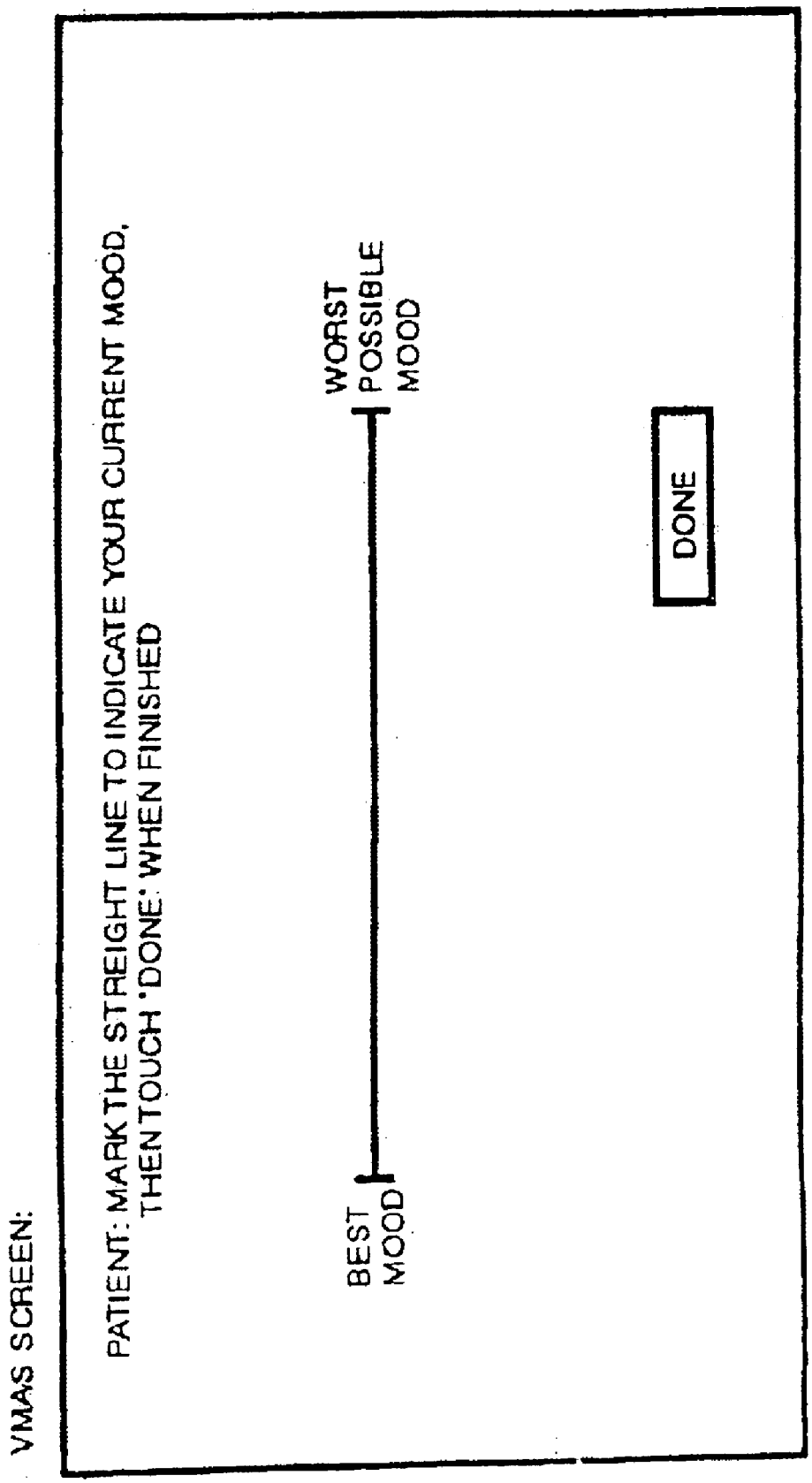
FIG. 13 shows a Visual Mood Analog Scale Screen.

The COMPAT method, typically performed as part of one or more software applications, at least some of which are performed by the COMPAT device, comprises a series of input forms for completion typically by a patient, a nurse, and a physician. Others may complete the forms, sometimes on behalf of the patient, the nurse, and the physician. The software application may, for example, present three input forms, one for the patient, one for the nurse, and one for the physician. The patient form typically comprises a series of forms for administering patient pain assessment questions such as, for example, questions of the PQ battery, each presented one at a time on the screen. The PQ battery may include the VPAS, VMAS, PS and/or PR scales described herein. Completion of the PQ item by the patient typically causes the response to be stored in a database in computer memory, and preferably in a storage device, for example a hard drive, and iterates the program to the next PQ item. When all PQ items are completed, in this example, all four PQ forms, the device 'sleeps' until the next scheduled completion time, FIGS. 12–15 illustrate four PQ item screens that can be used for the current invention, either singly or in combination: the Visual Pain Analog Scale (VPAS; FIG. 12), the Visual Mood Analog Scale (VMAS; FIG. 13), and the two Category Scales; Pain Severity (PS, FIG. 14) and Pain Relief (PR, FIG. 15). Certain embodiments of the current invention comprise other pain-related questions in addition to, or instead of, any or all of the four question batteries described above.

The nurse input screens may be protected by a security code, and may provide input forms for demographic information and treatment information. For example, but not intended to be limiting, the nurse input screens may comprise two input forms. The first form may provide input fields for entry of patient demographic data, including hospital code number and medical status information (e.g., ICD or CPT procedure codes, status pre/post treatment). In certain embodiments, these choices may be selected by the hospital and/or the institution. The second nurse form may comprise treatment screens. The screens may provide pull-down menus from which a nurse may select drug names and drug doses to record their administration; preferably these window selections having been entered on the physician screen (see hereinafter). The nurse input screen may also present the nurse with a checklist of signs and symptoms for the nurse to endorse if present (such as the signs of the opiate withdrawal syndrome) and vital signs information (such as blood pressure, heart rate, respiration rate, and the like).

The physician screen typically provides input forms and output forms. For example, but not intended to be limiting, a physician screen may present one input form and allow selection of the output summary graph. The input form may provide a physician 'order', by allowing the physician to select prescription drugs and dose, route and time limits for their administration, and to determine the frequency of PQ delivery to the patient. For example, but not intended to be limiting, the PQ may be delivered every 1 minute, 5 minutes, 10 minutes, 15 minutes, 30 minutes, 60 minutes, 2 hours, 4 hours, 8 hours, 16 hours, 24 hours, and 1 week; preferably it is determined every hour and more preferably, every waking hour. The physicians 'order' may in addition contain defaults of the standard approved protocol treatments for the ward in addition to the unique physician's orders for the selected patient.

Figure 16:
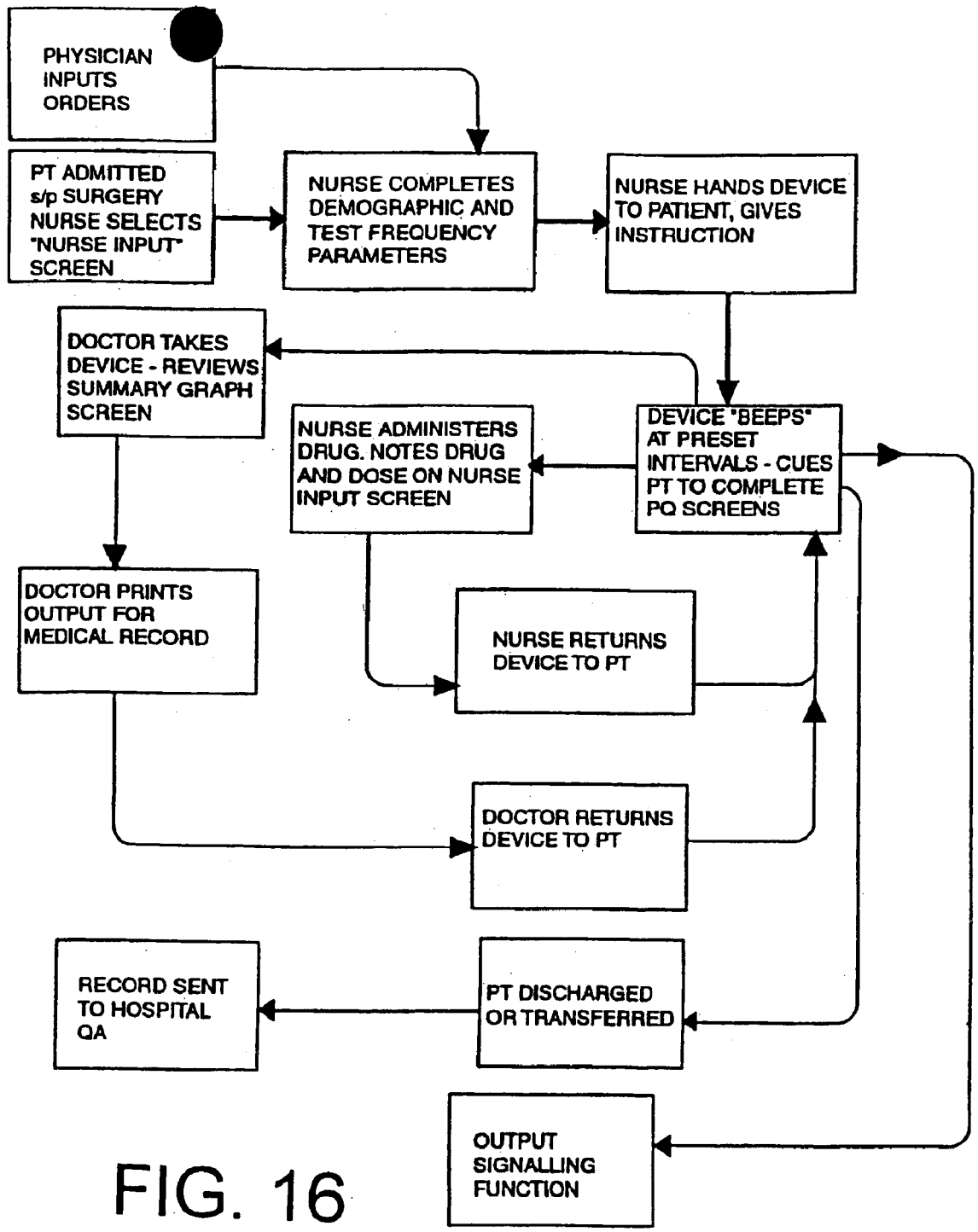
FIG. 16 is a flowchart exemplifying use of the COMPAT device.

Referring now to FIG. 16, a non-limiting example of a method using the COMPAT software includes the following:

(1) a nurse completes demographic details;

(2) a physician completes the initial order screen;

(3) a patient completes the PQ when the device signals the patient, for example 'beeps,' at the preset interval;

(4) when the nurse administers a drug, s/he completes the nurse input screen; and, (5) when the physician arrives at the bedside—or in some embodiments, remotely from their office—s/he selects the output summary graph, reviews the case and considers treatment changes.

Figure 17:
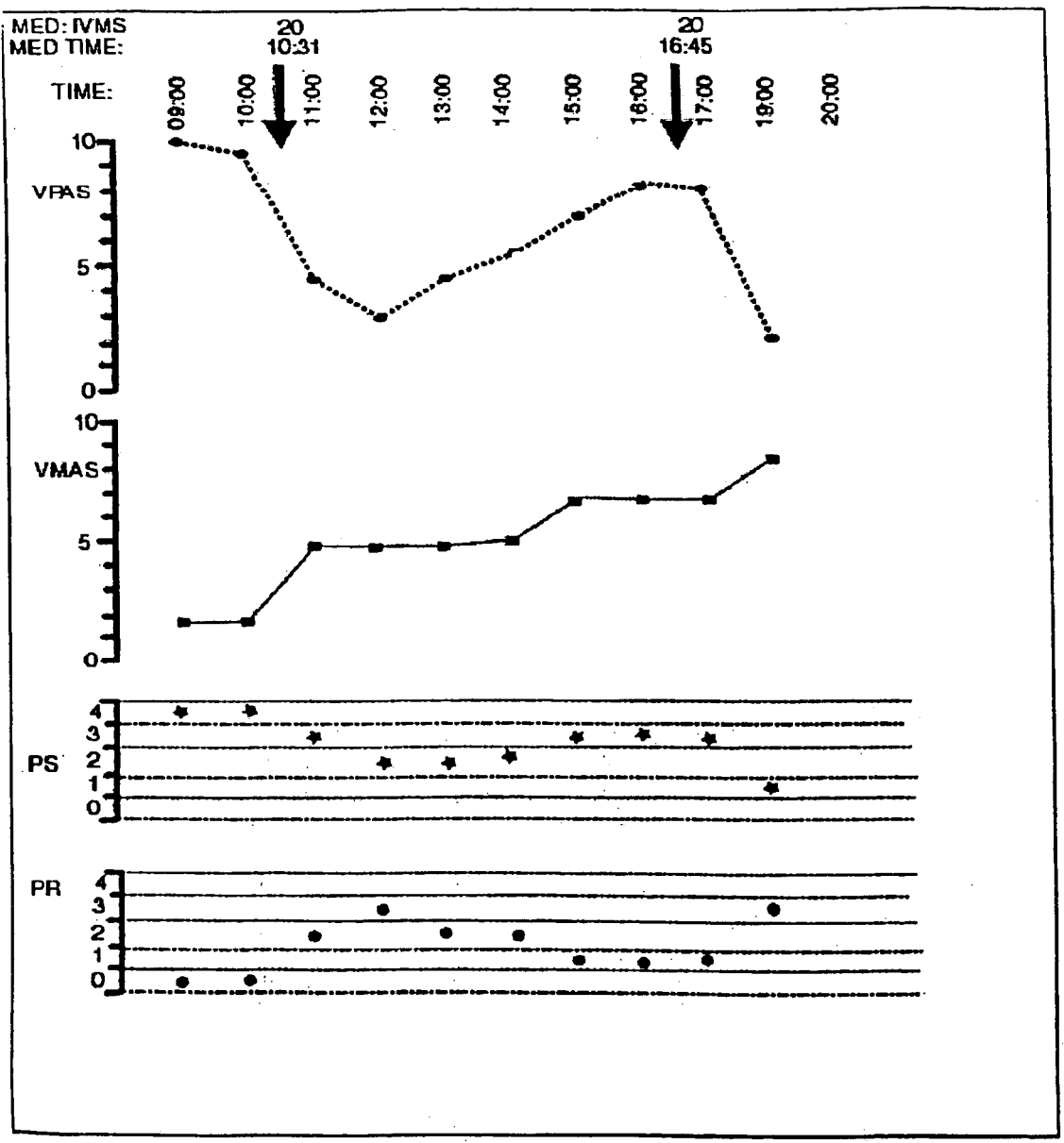
FIG. 17 is an example of an output summary graph.

A non-limiting example of a summary report is shown in FIG. 17. The summary report typically includes a graphical representation (i.e., summary graph) of patient pain questionnaire results over time. The summary report may include other statistical information and typically includes information regarding timing and composition of treatments. Additionally, patient demographic data as well as physician and nurse information may be included on the summary report.

In certain embodiments of the COMPAT software method of the current invention, the software method analyzes the patient pain data entered into the system and, where appropriate, fulfills nurse call functions if pain relief is inadequate. Additionally, the software may serve other integrated purposes within the ward patient care plan. Nurse call functions are triggered by the software where the patient pain data violates certain criteria. For example, but not intended to be limiting, the COMPAT software may trigger a nurse or physician notification feature if an individual's pain score increases by more than about 10%, 15%, 20%, 25%, 30%, 50%, 75%, or 100% within about 30 minutes, 60 minutes, or 2 hours. In one embodiment the notification trigger is set at a pain score increase of more than about 25% within about 2 hours. In other embodiments, the notification trigger is activated where an individual's pain score fails to decrease more than about 5%, 10%, 20%, 25%, or 50%, preferably about 10%, in about 30 minutes, about 60 minutes, about 2 hours, about 4 hours, and about 8 hours, preferably about 60 minutes following a pain relief procedure such as a drug administration.

In certain embodiments the notification trigger is activated based on statistical analysis. Many statistical analysis techniques are known in the art for comparing values and for detecting trends in values over time. For example, the notification trigger may be activated based on a statistically significant change in an individual's pain score, or based on control charting runs rule violations.

In certain embodiments, analysis of results using appropriate criteria may be used to trigger other effector functions. For example, but not intended to be limiting, the effector function may be autodelivery of pain medication using PCA (Patient Controlled Analgesia) controllers. Patient Controlled Analgesia controllers are well-known in the art of pain management. The amount of pain medication to be delivered can be determined by one of ordinary skill. Typically, the amount of pain medication is such that results of the pain questionnaire are improved with respect to the amount of pain felt by a patient.

A wide variety of commercial computer programming languages may be used to write the COMPAT software of the current invention. For example, but not intended to be limiting, Visual Basic or C++ may be used to write the COMPAT software. The COMPAT software is written in languages (e.g., C++, Visual Basic, Excel, and Access database) designed for the operating system resident on the hardware, for example Windows NT, UNIX or LINUX. In terms of software forward-compatibility, the software chosen is preferably fully supported and fully forward compatible.

In another aspect, the current invention provides a patient pain management system that comprises:

a) a patient communication device comprising a patient device microprocessor effective for executing a pain questionnaire software application, such as the COMPAT software described above; and b) a data processor capable of automatically communicating with the patient communication device. In certain embodiments, the data processor is a separate processor from the patient device microprocessor.

More specifically, the COMPAT software application described above is carried out using a COMPAT device that is typically connected to a data processor, such as a computer processor running a software application for processing an input signal from the COMPAT device. A patient pain management system of the current invention comprises the COMPAT device and the data processor with which the COMPAT device communicates. The computer processor may be associated with a computer such as, for example, but not limit to, a stand-alone personal computer, a networked personal computer, a network server and/or client, the COMPAT device itself, or an Internet server. The COMPAT device is typically a stand-alone portable device, for example a portable bedside device, for performing the COMPAT functions. In certain embodiments the device has remote connectivity to remote base stations by, for example, but not limited to, (1) network connection to central nurse's station and doctor's office, and/or (2) modem and/or Internet link to a server for remote use, including hospice and home care.

In one embodiment, the COMPAT device is comprised of independent low-voltage platforms at each patient's bedside. The COMPAT device typically comprises a microprocessor that runs a software application that administers the COMPAT method described above. For example, a portable digital device such as a cellular phone, a notebook personal computer, a personal digital assistant (PDA), especially a Palm™ device, with a touch-sensitive LCD screen. Other input devices may be used for the current invention besides a touch-sensitive LCD screen, such as, for example, voice input devices or keyboards. The COMPAT device is typically capable of delivering the pain questionnaire at the appropriate time points without intervention by medical personnel.

The COMPAT device may provide other functions besides those associated with the COMPAT method described above. For example, the COMPAT device may also perform functions associated with stimulating and measuring a pain response, such as pain threshold or pain tolerance, of a patient. Furthermore the COMPAT device may provide any functionality typically present in hand-held computer devices such as cellular telephones, personal digital assistants etc. In certain preferred embodiments, the COMPAT device does not perform a function associated with stimulating a pain response in a patient. In fact, the COMPAT device may run as a stand-alone device dedicated primarily, or solely, to performing the COMPAT method described above.

The touch screen, when present, is preferably lightweight, washable, cleanable, and well illuminated. The device may use a low voltage DC current transformer or batteries.

The COMPAT device preferably has one or more, and more preferably a majority, of the following characteristics:

(1) a screen more than about 10 cm wide, so that 10 cm lines of the VPAS and VMAS are reproduced full size;

(2) the screen is backlit to enable it to be easily seen in variable day and night light conditions of the ward, recovery room and intensive care unit.

(3) a touch-screen interface that is brightly illuminated;

(4) a disposable clear plastic over-wrap encapsulating preferably substantially the entire device, typically for cleanliness;

(5) a database stored in a robust medium with appropriate backup provisions in order to survive, unforeseen power disconnection;

(6) an audible alarm to alert a patient when a pain questionnaire should be conducted, wherein the audible alarm preferably is both loud and variable so that its tone can be changed when it too closely resembles that of another patient alarm; and (7) a visual signal accompanying the audible alarm so that the patient is cued to the correct device at the correct time.

The device in certain embodiments may have a keyboard, or other input devices; such devices are not however required.

Data from the device is typically capable of being manually downloaded to a nursing station or a physician office base station. The base station typically comprises a data processor which is capable of processing the data and preferably communicating with a database wherein the data is stored. For the current invention, this manual transfer of data from the COMPAT device to the data processor at the base station, as well as automated methods of transfer are non-limiting examples of communication between COMPAT device and the data processor. In certain embodiments, the software data analysis functions for generating the summary report, typically performed by the data processor, may be performed via the COMPAT device itself, a nurse's station computer, and/or a physician office base station.

The device and the data processor to which it communicates, directly or indirectly, typically contain microprocessors, for example Pentium™-based microprocessors.

The device of the current invention typically includes an operating system, for example a Microsoft Windows™ operating system, and a database, for example a Microsoft Access™ database, for use with the COMPAT software described hereinabove.

In certain embodiments the COMPAT device employs wired or wireless networking methods to directly link multiple units to base-stations in nurse and doctor's offices. For example, a networked group of many devices, for example twenty or more COMPAT devices, communicate through the network with a data processor at a central nurse's station. Certain embodiments may be capable of electro-magnetic radiation connectivity such as radio or infra red, or USB uplink to printers and base stations.

In certain embodiments, especially where the pain management system comprises network connectivity, additional functions can be provided, such as nurse-notification. For example, the system may provide a functionality that alerts a nurse or physician, for example by a remote device such as a pager, if an individual's pain scores trigger an effector function, according to software functions described hereinabove.

In certain preferred embodiment, the COMPAT device may be linked with PCA (Patient Controlled Analgesia) controllers to autoadminister analgesic injections. In these embodiments, the PCA controller may be considered part of the patient pain monitoring system. In yet another embodiment, the pain monitoring system of the current invention can fulfill nurse call functions if pain relief is inadequate, and serves other integrated purposes within the ward patient care plan.

The following examples are provided by way of illustration and not limitation to enable one skilled in the art to appreciate the scope of the present invention and to practice the invention without undue experimentation.

EXAMPLE 1

Feedback Control Procedure for HBD

Figure 18:
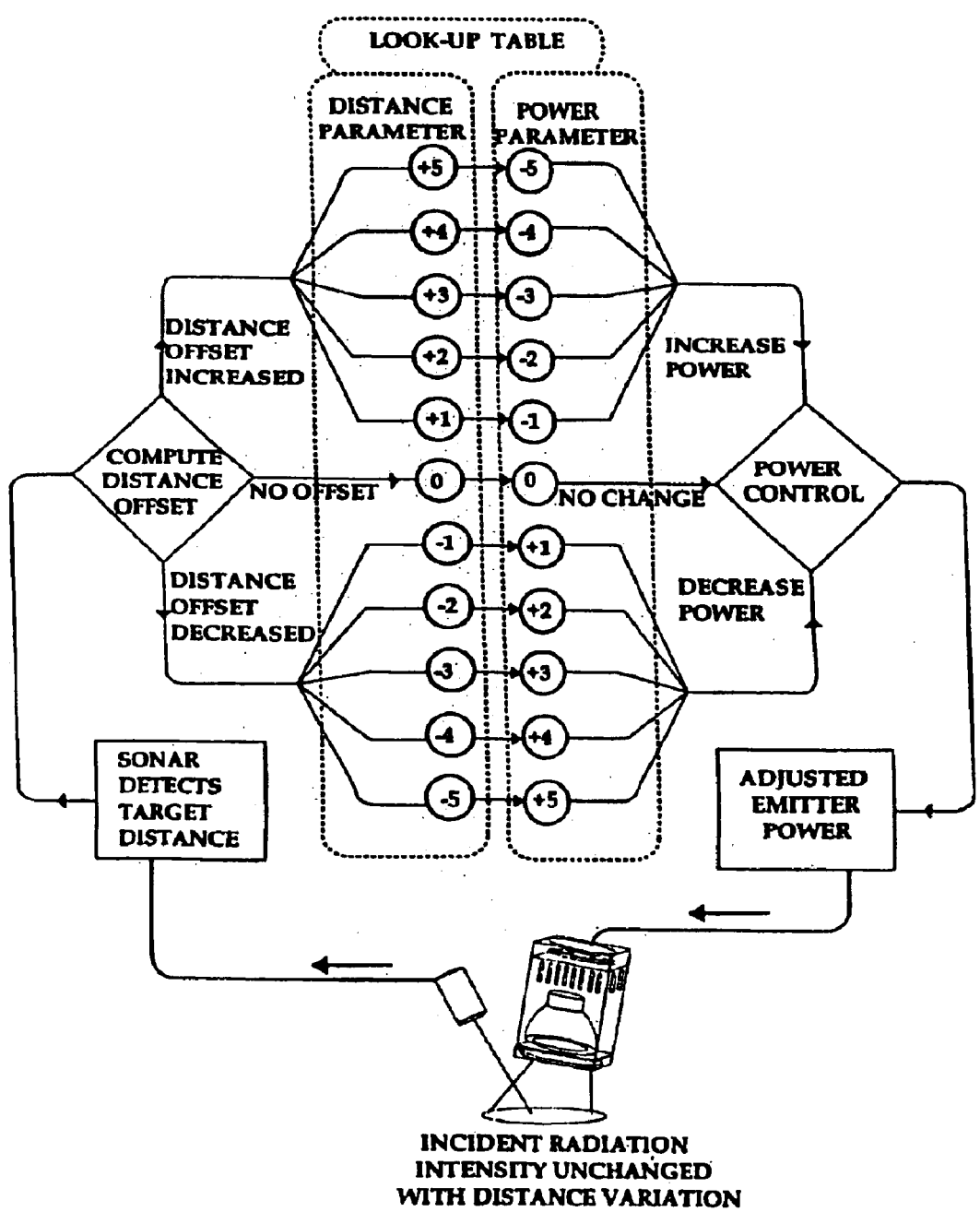
FIG. 18 illustrates the logic flowchart employed by the power control circuit for the device of FIG. 9A in responding to the sonar control circuit, to maintain the radiation incident at the target at the desired constant intensity with changing distance.

Demonstrated in the present example, a preferred embodiment provides a stable stimulus temperature at the target site and counters the effect of the tendency of a hand-held unit to move or change position under operator control upon the emission received by a target. The device achieves this automatic compensation for the effect of distance change by means of a look-up table procedure in the power control software. The process, illustrated in the flow diagram FIG. 18, was investigated using an optical bench apparatus.

Thus, regardless of tremor or other movement in the hand of the operator, the effect of the stimulus beam on target temperature is held substantially constant—at the value previously defined as producing the nominal temperature at the nominal distance of the arm-mounted version regardless of distance (within limits). Should the operator attempt to use the device outside of these limits the sonar will disengage the power to the beams, as a safety measure and to prevent unreliable measurements.

Demonstration of the Process:

Definition of the "optimal" power at the "optimal" or nominal distance was derived for the arm-mounted device, (called herein the "Basic HBD" or "Phase 0" model) using the optical bench apparatus. Under the experimental procedure followed, twenty seconds of thermal irradiation were applied to a copper disc target by either the Basic HBD or by the present, improved, hand-held sonar regulated HBD (called herein the Phase 2, Phase 2B or P2B HBD) at the optimal operating distance and the sensor temperature was noted at 0.4 sec intervals.

Static (Non-moving) Testing:

Mounting the Basic HBD device in the apparatus, the copper disc target was adjusted to the standard nominal operating distance of the device (i.e. 2.0 inches) and triplicate readings of temperature recorded over 20 seconds on the associated recording apparatus at 0.4 sec intervals. The improved sonar-regulated HBD (the "Phase 2B" HBD) was then mounted in place of the Basic device and the sonar-regulating functionality was disabled. Next, with the sonar-controls of the sonar-regulated HBD inoperative, (i.e., no feedback control), a range of different power values were manually input to the power control software of the hand-held sonar-regulated HBD device at different distances from the sensor, to determine by trial-and-error the appropriate power settings that generated at each distance the same target temperature as did the Basic HBD device at the single, optimal distance at which that device is conventionally used. Power settings were obtained at 0.1 inch increments over a one-inch range centered on the 'optimal' distance for the focal geometry. The data are illustrated in FIG. 19.

Figure 19:
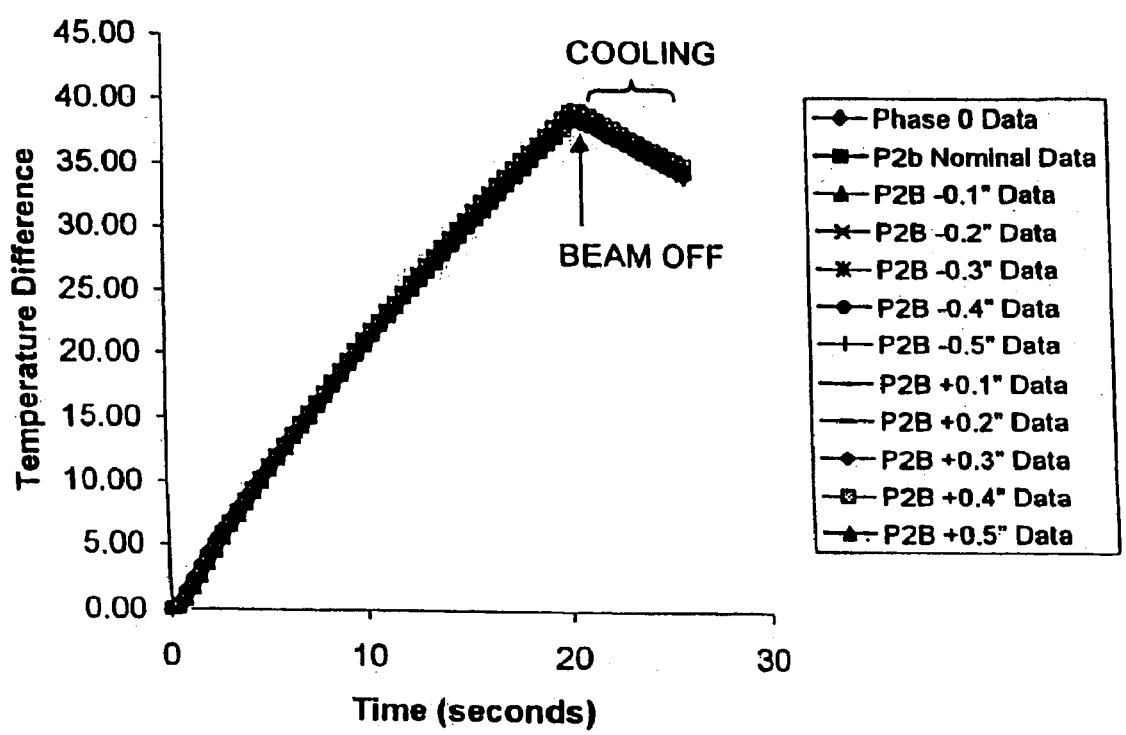
FIG. 19 illustrates the effect of incident radiation on a target emitted by the basic HBD at a single distance, and compares this with the effect resulting from the hand-held sonar embodiment of FIG. 9A with sonar compensation disabled, at eleven different static (nonmoving) distances, each operated at a different beam power, to provide a calibration of the sonar-controlled device.

From FIG. 19 it can be seen that by means of the above optical bench method, power values ('Beam Values' of the Pulse Width Modulation power controls) were derived which enabled the improved sonar-regulated HBD (called P2B in the figure) with sonar compensation functionality disabled, to achieve—at any one of eleven distances, in the present case—the same heating curve providing 1.93° C./sec as had been previously achieved with the Basic HBD at the single optimal distance (Phase 0 HBD, in the figure). There was no statistical difference between Basic HBD temperature curves and any of the sonar-regulated HBD-generated curves at any distance ($p>0.05$).

Figure 20:
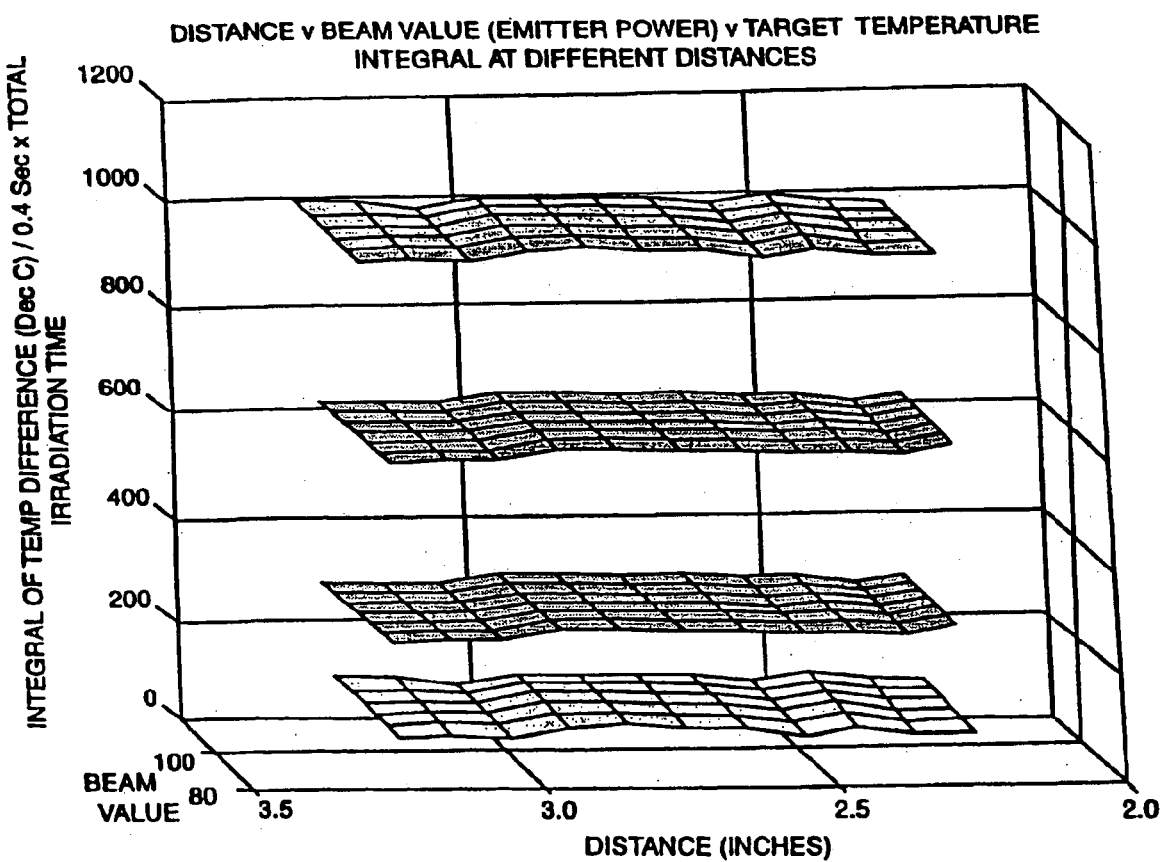
FIG. 20 illustrates the dependence of the cumulative target temperature (integral) upon both beam value (emitter power) and distance from the target under static (nonmoving) conditions.

Examining the precision and stability with which the emitter control circuitry and software of the sonar-regulated HBD device achieves stable temperature control by varying power ('beam value') with time fixed and at different distances, FIG. 20 illustrates the integrals of this relationship, which are as expected: the almost planar shape of the integral surfaces reveal good emitter control at each of the distances employed in this test and illustrate the dependence of target temperature on both power and distance.

Figure 21:
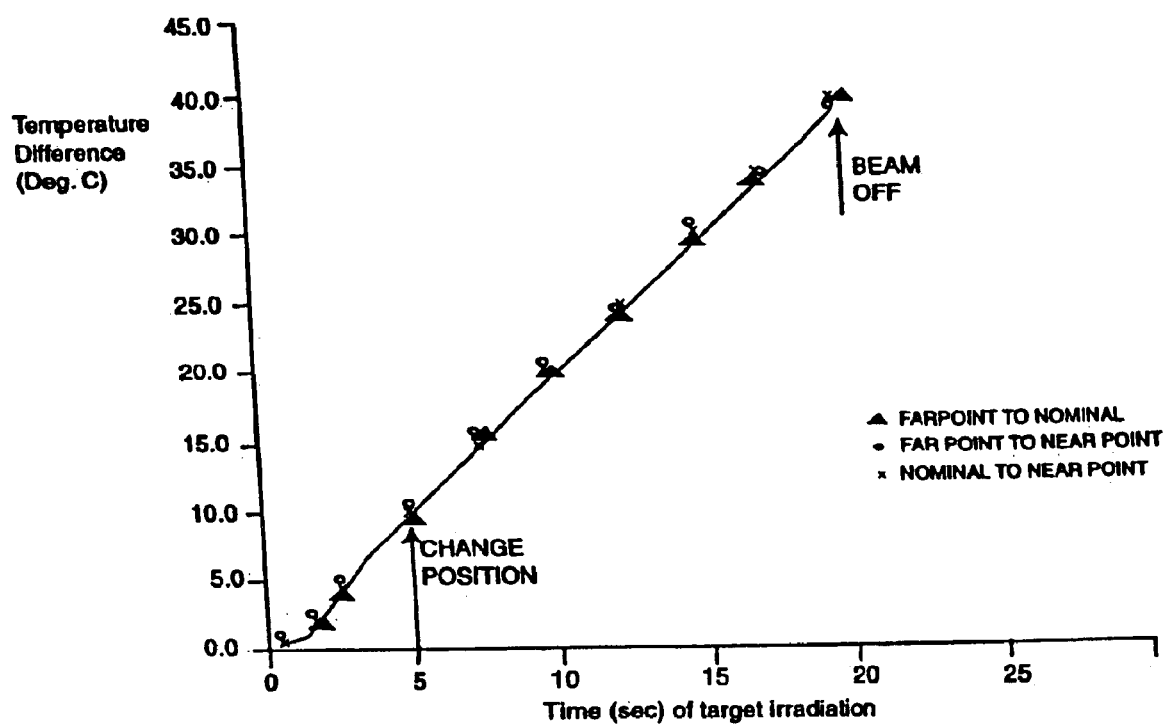
FIG. 21 illustrates the effect of incident radiation on a target produced by the hand-held dolorimeter of FIG. 9A with sonar compensation functionality enabled and the device dynamically moved. Over a 20 second irradiation of the target, the device is moved to different distances and the effect remains the same as is was achieved with the non-moving basic HBD.

Dynamic Testing:

The improved Sonar HBD was then tested with sonar feedback control activated. The above-derived power values from the optical bench study illustrated in FIG. 19 were then input as parameters into the power control feedback software, so that the device would autoregulate power output in response to detected changes in sonar-ranging distance to the target sensor according to the algorithm of FIG. 18. The optical bench procedure was then employed to dynamically vary the HBD-target distance, in order to detect and measure such dynamic autoregulation: the HBD being driven either away from or toward the target during the 20 second heating period. FIG. 21 illustrates these data with the improved Sonar-regulated HBD being moved toward the target at the fifth second (arrow in FIG. 21) from the far point to the "nominal" operating distance, then from the far point to the near point, and from the nominal distance to the near point. All three curves (which are the means of replicates) are essentially coincident ($R^2=0.98$, $p>0.05$). Thus, the sonar controlled feedback regulation of beam power with distance successfully auto-regulates a substantially constant heating profile at the target, and, further, regardless of distance and regardless of movement, the improved hand-held Sonar HBD achieves the same heating characteristics as the Basic HBD device within the limits tested.

The invention now being fully described, it will be apparent to one of ordinary skill in the art that many changes and modifications can be made thereto without departing from the spirit or scope of the invention as set forth therein. The examples described herein illustrate the methods and devices of the invention. These examples are intended to be merely illustrative of the present invention, and not limiting thereof in either scope or spirit. Those skilled in the art will readily understand that variations of the components, methods, steps, and devices described in these examples can be used. All references cited herein, as well as application No. PCT/US00/41672, Filed Oct. 26, 2000, are incorporated by reference in their entirety.

What is claimed is:

1. A method for monitoring pain of a patient, said method comprising:
    a) providing a patient communication device;
    b) providing a data processor capable of communicating with the patient communication device;
    c) delivering a pain questionnaire to the patient at each of a series of time points using the patient communication device to generate pain questionnaire results;
    d) communicating the pain questionnaire results to the data processor; and
    e) processing the pain questionnaire results using the data processor, thereby monitoring the pain of a patient, wherein the pain questionnaire is selected from the group consisting of a Visual Pain Analog Scale, a Visual Mood Analog Scale, a Pain Severity Scale and a Pain Relief Scale.

2. The method of claim 1, wherein the pain questionnaire comprises at least two members selected from the group consisting of a Visual Pain Analog Scale, a Visual Mood Analog Scale, a Pain Severity Scale and a Pain Relief Scale.

3. The method of claim 1, wherein the pain questionnaire comprises at least three members selected from the group consisting of a Visual Pain Analog Scale, a Visual Mood Analog Scale, a Pain Severity Scale and a Pain Relief Scale.

4. The method of claim 1, wherein the pain questionnaire comprises a Visual Pain Analog Scale, a Visual Mood Analog Scale, a Pain Severity Scale and a Pain Relief Scale.

5. The method of claim 1, wherein the patient communication device comprises a patient device microprocessor, wherein the communicating is performed automatically, and wherein the data processor is a separate processor from the patient device microprocessor.

6. The method of claim 1, further comprising triggering an effector function based on the process pain questionnaire results.

7. The method of claim 1, wherein the delivering of the pain questionnaire is performed by the patient without assistance of medical personnel.

8. The method of claim 1, wherein the delivering of the pain questionnaire is performed other than as part of a pain-stimulation or sensory stimulation procedure, and without stimulating a pain response in the patient.

9. A method for monitoring pain of a patient, said method comprising:
    a) providing a patient communication device, wherein the patient communication device includes a heat beam dolorimeter;
    b) providing a data processor capable of communicating with the patient communication device;
    c) delivering a pain questionnaire to the patient at each of a series of time points using the patient communication device to generate pain questionnaire results;
    d) communicating the pain questionnaire results to the data processor; and
    e) processing the pain questionnaire results using the data processor, thereby monitoring the pain of a patient.

10. A patient pain management system comprising:
    a) a patient communication device comprising a patient device microprocessor effective for executing a pain questionnaire software application, wherein the patient communication devise includes a heat beam dolorimeter; and
    b) a data processor effective for automatically communicating with the patient communication device.

11. The system of claim 10, wherein the heat beam dolorimeter utilizes a sonar ranging sensor.

* * * * *